(12) United States Patent
Assell et al.

(10) Patent No.: US 9,662,124 B2
(45) Date of Patent: May 30, 2017

(54) SACROILIAC FUSION SYSTEM

(71) Applicant: ZYGA TECHNOLOGY, INC., Minnetonka, MN (US)

(72) Inventors: Robert Assell, St. Paul, MN (US); Jeremy Carr, Lauderdale, MN (US); Eugene Dickhudt, Lino Lakes, MN (US); Thomas Berg, Centerville, MN (US); Brian Beaubien, St. Paul, MN (US)

(73) Assignee: Zyga Technology, Inc., Minnetonka, MN (US)

( * ) Notice: Subject to any disclaimer, the term of this patent is extended or adjusted under 35 U.S.C. 154(b) by 91 days.

(21) Appl. No.: 14/721,753

(22) Filed: May 26, 2015

(65) Prior Publication Data
US 2016/0128838 A1 May 12, 2016

Related U.S. Application Data

(60) Division of application No. 13/465,612, filed on May 7, 2012, now Pat. No. 9,161,763, which is a (Continued)

(51) Int. Cl.
*A61F 2/30* (2006.01)
*A61B 17/70* (2006.01)
(Continued)

(52) U.S. Cl.
CPC ...... *A61B 17/1671* (2013.01); *A61B 17/1617* (2013.01); *A61B 17/1664* (2013.01);
(Continued)

(58) Field of Classification Search
CPC ....... A61F 2/30988; A61F 2002/30995; A61B 17/1617; A61B 17/1671; A61B 17/1664; A61B 17/320016
See application file for complete search history.

(56) References Cited

FOREIGN PATENT DOCUMENTS

WO 2008/054752 A2 5/2008

OTHER PUBLICATIONS

Japanese Office Action received in JP Applic. No. 2014-509508, Mar. 15, 2016, 5 pages.

*Primary Examiner* — Christian Sevilla
(74) *Attorney, Agent, or Firm* — Michael A. Bondi; Moss & Barnett

(57) ABSTRACT

A method of performing an orthopedic procedure in the sacroiliac region. At least one aperture is formed that at least partially extends through at least one of an ilium and a sacrum. An undercutting system is at least partially inserted into the aperture. The undercutting system includes an insertion apparatus, a probe assembly and a cutting assembly. The probe assembly is moved with respect to the insertion apparatus from a retracted position to an extended position. The probe assembly is manipulated within a joint between the ilium and the sacrum while the probe assembly is in the extended position. The cutting assembly is moved with respect to the insertion apparatus from a retracted position to an extended position. The cutting assembly is sharper than the probe assembly. The cutting assembly is manipulated within the joint between the ilium and the sacrum while the cutting assembly is in the extended position to form a fusion region. The undercutting system is removed from the aperture.

21 Claims, 17 Drawing Sheets

Related U.S. Application Data continuation-in-part of application No. 12/938,976, filed on Nov. 3, 2010, now Pat. No. 8,348,950.

(60) Provisional application No. 61/292,021, filed on Jan. 4, 2010, provisional application No. 61/610,759, filed on Mar. 14, 2012, provisional application No. 61/482,899, filed on May 5, 2011.

(51) Int. Cl.
| | | |
|---|---|---|
| *A61B 17/16* | (2006.01) | |
| *A61B 17/32* | (2006.01) | |
| *A61B 17/84* | (2006.01) | |
| *A61B 90/00* | (2016.01) | |
| *A61B 17/3203* | (2006.01) | |
| *A61B 17/00* | (2006.01) | |
| *A61B 17/3207* | (2006.01) | |

(52) U.S. Cl.
CPC .......... *A61B 17/32002* (2013.01); *A61B 17/320016* (2013.01); *A61B 17/7055* (2013.01); *A61B 17/84* (2013.01); *A61F 2/30988* (2013.01); *A61B 17/1604* (2013.01); *A61B 17/1608* (2013.01); *A61B 17/1624* (2013.01); *A61B 17/1633* (2013.01); *A61B 17/3203* (2013.01); *A61B 2017/0046* (2013.01); *A61B 2017/00261* (2013.01); *A61B 2017/00464* (2013.01); *A61B 2017/00469* (2013.01); *A61B 2017/00867* (2013.01); *A61B 2017/320004* (2013.01); *A61B 2017/32006* (2013.01); *A61B 2017/320012* (2013.01); *A61B 2017/320028* (2013.01); *A61B 2017/320032* (2013.01); *A61B 2017/320791* (2013.01); *A61B 2090/031* (2016.02); *A61B 2090/062* (2016.02); *A61F 2002/30995* (2013.01)

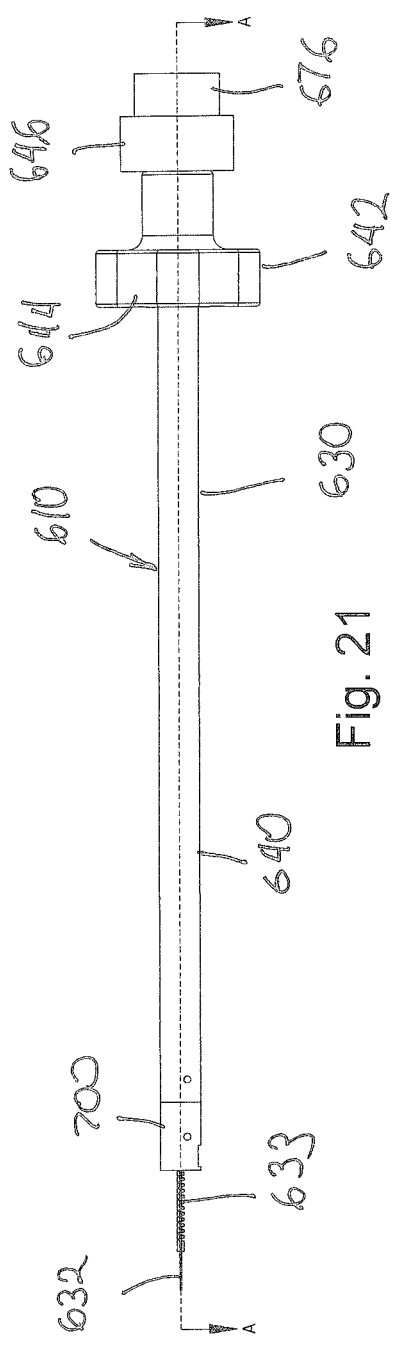
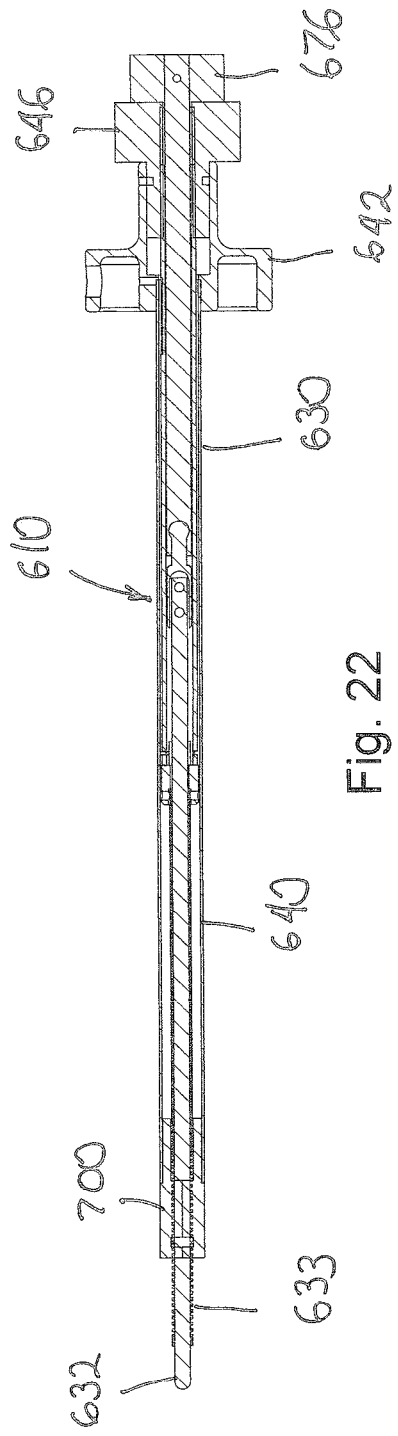
Fig. 21
Fig. 22

SACROILIAC FUSION SYSTEM

REFERENCE TO RELATED APPLICATION

This application is a divisional of U.S. application Ser. No. 13/465,612, which was filed on May 7, 2012, which is a continuation-in-part of U.S. application Ser. No. 12/938,976, which was filed on Nov. 3, 2010, which claims the benefit of priority from Application Ser. No. 61/292,021, filed Jan. 4, 2010. This application claims the benefit of priority from Application Ser. No. 61/610,759, filed Mar. 14, 2012, and Application Ser. No. 61/482,899, filed May 5, 2011. The entire content of these U.S. applications are incorporated herein by reference.

FIELD OF THE INVENTION

An embodiment of the invention is directed to a method for treating patients experiencing sacroiliac joint pain. More particularly, the invention relates to a system for preparing a space between the sacrum and the iliac to facilitate sacroiliac joint fusion.

BACKGROUND OF THE INVENTION

The sacroiliac joint is located at the intersection of the ilium, the upper bone of the pelvis, and the sacrum at the base of the spine. One of the primary functions of the sacroiliac joint is to provide shock absorption of pressures put on the spine.

Certain persons experience pain in the sacroiliac joint. This pain may result from a variety of causes, examples of which include injuries, incorrect vertebra fusion during pre-birth development and effects of pregnancy.

If initial efforts to reduce the pain in the sacroiliac joint through physical therapy and/or steroid injections are not effective, surgery may be needed to fuse together the sacroiliac joint. One typical surgical technique involves forming an incision in the lower back over the sacroiliac joint. The articular cartilage is removed from both surfaces. This process is also called chondrectomy.

The sacrum and the ilium are held together with screws or a plate. Eventually, bone grows between the sacrum and the ilium to thereby fuse together the sacroiliac joint. Because of the challenges in accessing the surfaces of the sacrum and the ilium that will fuse together, this type of surgery may result in damage to tissue, nerves and/or blood vessels that surround the sacroiliac joint. Such damage may prevent the patient from fully realizing the benefits of the sacroiliac joint fusion and in some instances cause the patient to experience more pain after the sacroiliac joint fusion than before the sacroiliac joint fusion.

SUMMARY OF THE INVENTION

An embodiment of the invention is directed to a method of performing an orthopedic procedure in the sacroiliac region. At least one aperture is formed that at least partially extends through at least one of an ilium and a sacrum. An undercutting system is inserted at least partially into the aperture. The undercutting system includes an insertion apparatus, a probe assembly and a cutting assembly.

The probe assembly is moved with respect to the insertion apparatus from a retracted position to an extended position. When in the retracted position, the probe assembly is substantially within the insertion apparatus. When in the extended position, at least a portion of the probe assembly extends from the insertion apparatus. The probe assembly is manipulated within a joint between the ilium and the sacrum while the probe assembly is in the extended position.

The cutting assembly is moved with respect to the insertion apparatus from a retracted position to an extended position. When in the retracted position, the cutting assembly is substantially within the insertion apparatus. When in the extended position, at least a portion of the cutting assembly extends from the insertion apparatus. The cutting assembly is sharper than the probe assembly. The cutting assembly is manipulated within the joint between the ilium and the sacrum while the cutting assembly is in the extended position to form a fusion region. The undercutting system is removed from the aperture.

Another embodiment of the invention is directed to a method of performing an orthopedic procedure in the sacroiliac region. At least one aperture is formed that at least partially extends through at least one of an ilium and a sacrum. An undercutting system is inserted at least partially into the aperture. The undercutting system includes a cutting assembly.

The cutting assembly is moved to an extended position between the ilium and the sacrum where a portion of the cutting assembly extends beyond an outer periphery of the undercutting system. A fusion region is formed by moving the cutting assembly between the ilium and the sacrum. The cutting assembly is moved to a retracted position where the cutting assembly is substantially within the outer periphery of the undercutting system.

The undercutting system is removed from the aperture. A fastening device is inserted into the ilium aperture and the sacrum aperture. The fastening device retains the ilium and the sacrum in a stationary position with respect to each other.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 21 is a side view of an alternative configuration of an undercutting system for use in a sacroiliac fusion procedure.

FIG. 22 is a sectional view of the undercutting system of FIG. 6 taken along a line A-A in FIG. 21.

DETAILED DESCRIPTION OF THE PREFERRED EMBODIMENTS

Figure 31:
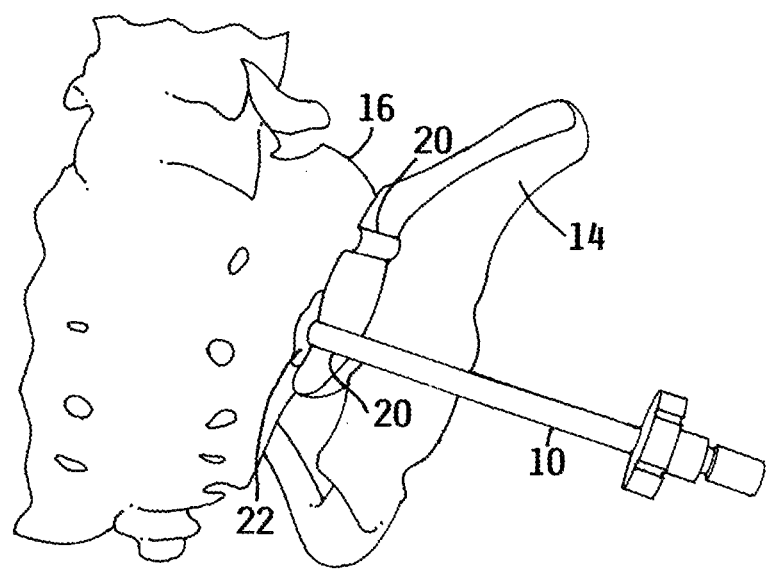
FIG. 31 is a partially cut away perspective view of an undercutting system being inserted into the aperture.

An embodiment of the invention is directed to an undercutting system 10, such as is illustrated in FIGS. 1-5. The undercutting system 10 may be used for preparing surfaces of the ilium 14 and the sacrum 16 for sacroiliac joint fusion, which are illustrated in FIG. 31. The undercutting system utilizes an aperture 20 formed in the ilium 14 to access a region 22 between the ilium 14 and the sacrum 16.

In certain embodiments, the aperture 20 may have a diameter of up to about 50 millimeters. In other embodiments, the aperture 20 may have a diameter of between about 5 millimeters and 20 millimeters.

The undercutting system 10 thereby enables tissue such as cartilage to be removed from the adjacent surfaces of the ilium 14 and the sacrum 16 and for at least a portion of the adjacent surfaces of the ilium 14 and the sacrum 16 to be removed or otherwise disturbed. This procedure may be referred to as preparing bleeding bone surfaces on the ilium 14 and the sacrum 16, which are more receptive to growing bone between them as part of sacroiliac joint fusion.

Thereafter, the ilium 14 and the sacrum 16 may be held in a stationary position with respect to each other such as by using a screw that is extended through the aperture 20, as is discussed in more detail below. Maintaining the ilium 14 and the sacrum 16 in the stationary position facilitates bone growth between the ilium 14 and the sacrum 16 to thereby fuse the sacroiliac joint.

Performing the sacroiliac fusion using the undercutting system 10 disclosed herein reduces the complexity of the sacroiliac fusion when compared to prior techniques used for sacroiliac fusion. Additionally, sacroiliac fusion performed using the concepts describe herein has the potential of fewer side effects because this process does not require the surgeon to work proximate the nerves and/or blood vessels, as is done with prior sacroiliac fusion techniques.

Furthermore, the apparatus and technique disclosed herein do not formally expose the sacroiliac joint to reduce the potential of infection. The time associated with preparing the surfaces of the ilium and the sacrum is also reduced when compared to the prior more invasive techniques used to prepare the sacroiliac joint for fusion.

In one embodiment, the undercutting system 10, may include an insertion apparatus 30 and a probe assembly 32 that extends from a distal end of the insertion apparatus 30, as illustrated in FIGS. 1-5.

The insertion apparatus 30 may include an elongated shaft 40 that is formed with a length that enables a proximal end thereof to be positioned outside of the patient's body while a distal end thereof is utilized to the prepare the region between the ilium 14 and the sacrum 16 for the sacroiliac fusion process. In certain embodiments, the length of the elongated shaft 40 is between about 15 centimeters and about 45 centimeters.

The elongated shaft 40 may be formed with a relatively small outer diameter to minimize a size of the aperture 20 that needs to be formed in the ilium 14. The larger the aperture 20 that is formed in the ilium 14, the greater the potential of the ilium 14 weakening to the point at which the ilium 14 is more susceptible to breakage. In certain embodiments, the outer diameter of the elongated shaft 40 is between about 6 millimeters and 20 millimeters.

The insertion apparatus 30 may also include a handle portion 42 proximate a proximal end thereof. The handle portion 42 enhances the ability to manipulate the insertion apparatus 30 such as insertion, rotation and withdrawal.

The handle portion 42 may have a diameter that is greater than a diameter of the elongated shaft 40. In certain embodiments, the handle portion 42 has a diameter of between about 2 centimeters and about 20 centimeters.

An outer edge of the handle portion 42 may have a plurality of concave regions 44 formed therein. The concave regions 44 enhance the ability to grip the handle portion 42 and thereby manipulate the insertion apparatus 30.

The insertion apparatus 30 may further include a control knob 46 that is used for extending and retracting the probe assembly 32. In one configuration of the insertion apparatus 30, the control knob 46 is rotatably mounted with respect to the insertion apparatus 30.

The control knob 46 may have a diameter that is different than a diameter of the handle portion 42. Forming the control knob 46 with a diameter that is different than a diameter of the handle portion 42 minimizes the potential that a person using the insertion apparatus 30 would inadvertently manipulate the insertion apparatus 30 or the control knob 46.

The control knob 46 may have a diameter that is less than a diameter of the handle portion 42. In certain embodiments, the control knob 46 has a diameter of between about 2 centimeters and about 20 centimeters.

An outer edge of the control knob 46 may have a plurality of concave regions 48 formed therein. The concave regions 48 enhance the ability to grip the control knob 46 and thereby manipulate the insertion apparatus 30.

Rotation of the control knob 46 in a first direction causes the probe assembly 32 to be extended from the distal end of the insertion apparatus 30. Rotation of the control knob 46 in a second direction, which is opposite the first direction, causes the probe assembly 32 to be retracted into the distal end of the insertion apparatus 30.

The insertion apparatus 30 may also include a lock screw 50 operably attached hereto. The lock screw 50 may be oriented generally transverse to the elongated shaft 40 and may be positioned proximate the handle portion 42. The lock screw 50 may threadably engage the elongated shaft 40.

The lock screw 50 may be positioned in an engaged position where a distal end of the lock screw 50 extends into the interior of the elongated shaft 40 until the distal end engages a shaft that extends between the probe assembly 32 and the control knob 46. The lock screw 50 thereby retains the shaft in a fixed position with respect to the elongated shaft 40 to prevent movement of the probe assembly 32 with respect to the insertion apparatus 30.

Rotating the lock screw 50 in an opposite direction causes the distal end to not engage the cutter shaft so that the shaft may be moved with respect to the elongated shaft 40 to move the probe assembly 32 between the extended and retracted positions.

Figure 1:
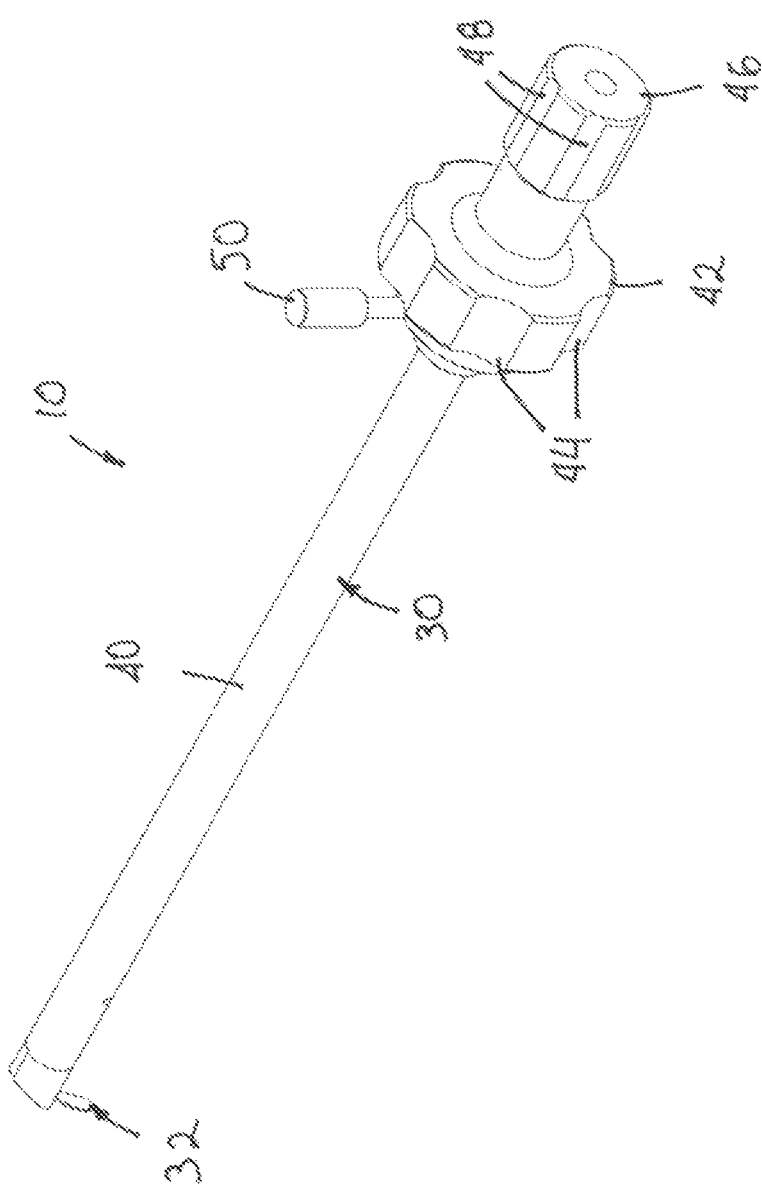
FIG. 1 is a perspective view of an undercutting system for use in a sacroiliac fusion procedure.
Figure 2:
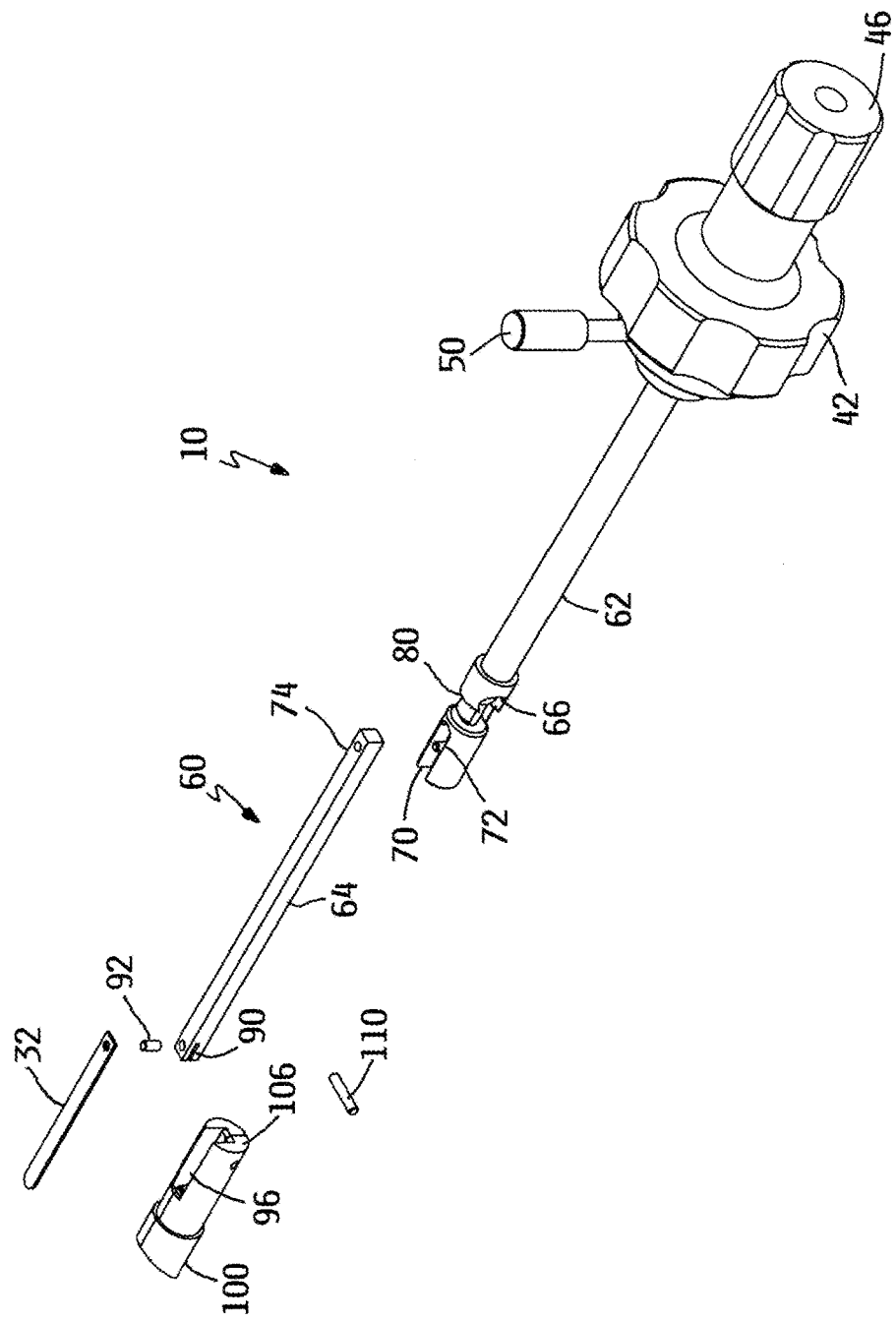
FIG. 2 is an exploded perspective view of the undercutting system.
Figure 3:
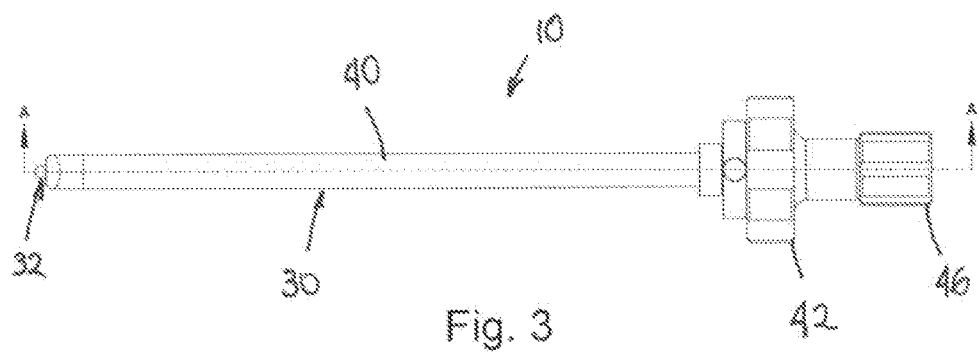
FIG. 3 is a top view of the undercutting system.
Figure 4:
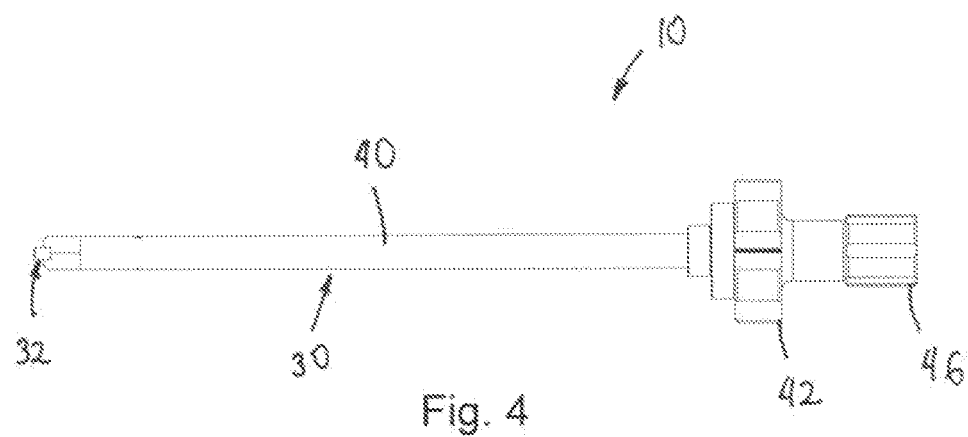
FIG. 4 is a bottom view of the undercutting system.
Figure 5:
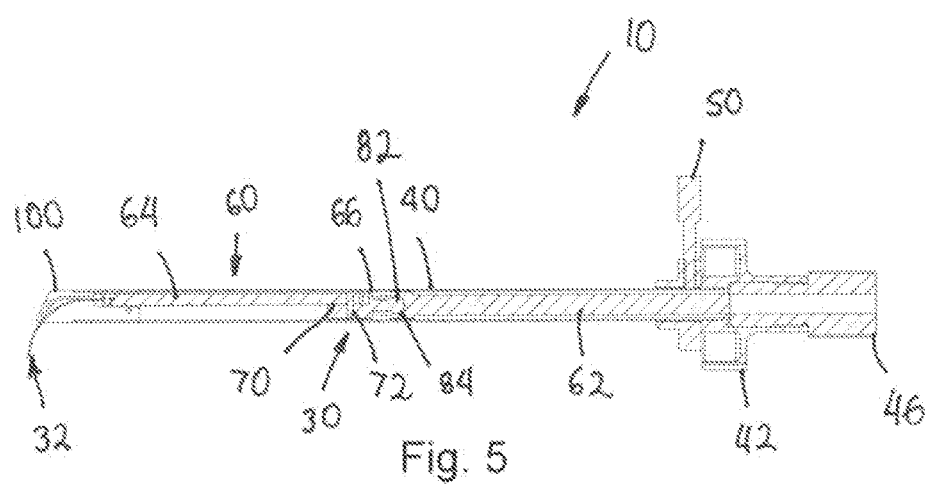
FIG. 5 is a sectional view of the undercutting system taken along a line A-A in FIG. 3.

Inside at least a portion of the elongated shaft 40 is a control mechanism 60 that operably attaches the probe assembly 32 to the other portions of the insertion apparatus 30, as most clearly illustrated in FIGS. 2 and 5. A primary function of the control mechanism 60 is to facilitate extension and retraction of the probe assembly 32.

When the probe assembly 32 is in the retracted position, the probe assembly 32 is within an outer periphery of the insertion apparatus 30. Using such a configuration enables the elongated shaft 40 to be inserted into the patient using a cannula having an inner diameter that is approximately the same as an outer diameter of the elongated shaft 40.

The control mechanism 60 may generally include a first attachment section 62 and a second attachment section 64. The first attachment section 62 is attached to the control knob 46. In one configuration, the first attachment section 62 is fixedly attached to the control knob 46 so that the first section 62 rotates when the control knob 46 is rotated.

The first attachment section 62 may have a length that is less than the length of the elongated shaft 40. In certain embodiments, the first attachment section 62 has a length that is approximately one-half of the length of the elongated shaft 40.

The first attachment section 62 may have a generally cylindrical shape with an outer diameter that is slightly smaller than an inner diameter of the elongated shaft 40, as most clearly illustrated in FIG. 5. Forming the first attachment section 62 with this shape facilitates rotating and sliding of the first attachment section 62 with respect to the elongated shaft 40.

A distal end of the first attachment section 62 has a connection mechanism 66 that facilitates attaching the second attachment section 64 to the first attachment section 62. In one such configuration, the connection mechanism 66 includes a recess 70 formed in the distal end. The recess 70 may have a width and a depth that is greater that a width and a depth of the proximal end of the second attachment section 64.

An attachment pin 72 may be provided in the recess 70 that enables the second attachment section 64 to engage the connection mechanism 66. In certain embodiments, the attachment pin 72 may be oriented generally perpendicular to the first attachment section 62.

An aperture 74 may be formed in the proximal end of the second attachment section 64. The aperture 74 may have a diameter that is slightly larger than a diameter of the attachment pin 72. Using such a configuration, the attachment pin 72 may extend into the aperture 74 to retain the first attachment section 62 in a fixed relationship with respect to the second attachment section 64.

Forming the connection mechanism 66 with preceding configuration allows the second attachment section 64 to be attached to the first attachment section 62 when the first attachment section 62 and the second attachment section 64 are not covered by the elongated shaft 40.

On the other hand, when the elongated shaft 40 is placed over first attachment section 62 and the second attachment section 64, the second attachment section 64 is retained in engagement with the first attachment section 62.

A person of skill in the art will appreciate that it is possible to attach the first attachment section 62 and the second attachment section 64 using different structures, which enable sliding and rotating of the first attachment section 62 and the second attachment section 64 with respect to the elongated shaft 40.

While the figures illustrate that a mechanical connection is provided between the probe assembly 32 and the other components of the undercutting system 10, it is also possible to utilize an electrical connection between the probe assembly 32 and the other components of the undercutting system 10. Such an electrical connection may utilize switches and actuators. It is also possible to use pneumatic and hydraulic systems to operably connect the probe assembly 32 and the other components of the undercutting system 10.

The mechanical connection between the probe assembly 32 and the other components of the undercutting system 10 provides a mechanical advantage that enables the probe assembly 32 to be extended from the insertion apparatus much more easily and controllably than if the undercutting system did not include the mechanical connection.

The invention thereby minimizes the potential of the probe assembly 32 being damaged during the insertion process. This invention also enhances the control over the size of the fusion region that is prepared.

The connection mechanism 66 may also include a ball-type connector 80 that attaches the connection mechanism 66 to the first attachment section 62. The ball-type connector 80 may include a ball-shaped extension 82 on the connection mechanism 66 and a recess 84 formed in the distal end of the first attachment section 62. The recess 84 has a shape that is generally complementary to the shape of the ball-shaped extension 82.

Similar to the attachment between the connection mechanism 66 and the second attachment section 64, the ball-type connector 80 allows the first attachment section 62 to be attached to the connection mechanism 66 when the first attachment section 62 and the connection mechanism 66 are not covered by the elongated shaft 40.

On the other hand, when the elongated shaft 40 is placed over first attachment section 62 and the connection mechanism 66, the ball-shaped extension 82 is retained in engagement with the recess 84.

The probe assembly 32 is attached to the distal end of the second attachment section 64. To accommodate using probe assemblies 32 having different lengths, the undercutting system 10 may be provided with more than one second attachment section 64 having different lengths. Alternatively or additionally, the undercutting system 10 may include more than one first attachment section 62 having different lengths. Using such a configuration enables one of the first attachment sections 62 and the second attachment sections 64 to be selected based upon the length of the probe assembly 32.

A benefit of using the ball-shaped extension 82 is that this connection mechanism enables the control handle to rotate such as when extending or retracting the probe assembly 32 with respect to the insertion apparatus 30 without having the probe assembly 32 rotate.

The distal end of the second attachment section 64 may have a recess 90 formed therein. The recess 90 may have a depth that is greater than a thickness of the proximal end of the probe assembly 32. The recess 90 may extend across at least a portion of a width of the second attachment section 64.

An attachment pin 92 may be provided in the recess 90 that enables the probe assembly 32 to engage the second attachment section 64. In certain embodiments, the attachment pin 92 may be oriented generally perpendicular to the second attachment section 64.

The second attachment section 64 may be formed with a height and a width that are both slightly smaller than a height and a width of a channel 96 that is formed in an end cap 100, which is discussed in more detail below. Forming the second attachment section 64 with these dimensions enables the second attachment section 64 to slide in the channel 96.

The cap 100 may be positioned in the distal end of the elongated shaft 40, as most clearly illustrated in FIG. 5. The cap 100 thereby seals the elongated shaft 40 to generally restrict tissue and fluid from entering the elongated shaft 40.

While it is possible for a distal end of the cap 100 to be oriented generally transverse to the elongated shaft 40, the distal end of the cap 100 may be oriented at an angle of less than about 90 degrees with respect to the elongated shaft 40. In certain embodiments, the distal end of the cap 100 is oriented at an angle of between about 45 degrees and about 60 degrees, as illustrated in FIG. 5.

As referenced above, the cap 100 has the channel 96 formed therein. Proximate the proximal end, the channel 96 may be generally aligned with but offset from a central axis of the elongated shaft 40. Proximate the distal end, the channel 96 may be oriented generally perpendicular to the central axis of the elongated shaft 40. The channel 96 thereby enables the probe assembly 32 to emerge from the insertion apparatus in a direction that is generally aligned with the surface of at least one of the ilium 14 and the sacrum 16.

Intermediate the proximal end and the distal end, the channel 96 is curved. The radius of curvature may be determined by a variety of factors. An example of one such factor is the flexibility of the portion of the probe assembly 32.

The channel 96 thereby causes the probe assembly 32 to be deflected such that when the probe assembly 32 extends from the cap 100, the probe assembly 32 is oriented in a direction that is generally transverse to the elongated shaft 40, as illustrated in FIG. 5, so that the probe assembly 32 can be extended into the region between the ilium 14 and the sacrum 16.

The cap 100 may have an aperture 106 that extends therethrough that is generally perpendicular to the axis of the elongated shaft 40. The elongated shaft 40 may also include an aperture that is generally aligned with the aperture 106 when the cap 100 is placed into the distal end of the elongated shaft 40. A pin 110 is extended through the aperture 106 and the aperture to thereby retain the cap 100 in a stationary position with respect to the elongated shaft 40.

The probe assembly 32 may have a variety of configurations, as is discussed in more detail herein. In one such embodiment, the probe assembly 32 may have an elongated configuration, as illustrated in FIGS. 2 and 6-8, where a proximal end 120 thereof is operably attached to the second attachment section 64 and a distal end 122 thereof extends from the undercutting system 10. This embodiment of the probe assembly 32 may be particularly useful for initial use to locate a surface of the ilium 14 and/or the sacrum 16.

The probe assembly 32 may have a thickness of up to about 2 millimeters. In certain embodiments, the probe assembly 32 may have a thickness of between about 0.4 millimeters and about 0.6 millimeters. Using the probe assembly 32 with the preceding dimensions provides the probe assembly 32 with flexibility in a distal-proximal direction while resisting twisting or otherwise deforming.

The resistance enables the probe assembly 32 to deflect in response to changes in the shape or orientation of the ilium 14 or the sacrum 16. Such deflection is important because it is much more difficult to cut through the bone of the ilium 14 and the sacrum 16 than the cartilage that is between the ilium 14 and the sacrum 16.

The configuration of the probe assembly 32 provides the probe assembly 32 with sufficient rigidity in a radial direction. Such a configuration allows the probe assembly 32 to resist deformation in response to rotation of the undercutting system 10 such as when the tissue between the ilium 14 and the sacrum 16 is contacted with the probe assembly 32.

The probe assembly 32 may have a width that is no greater than an inner diameter of the elongated shaft 40. Forming the probe assembly 32 with such a configuration enables the probe assembly 32 to be positioned substantially within a profile of the elongated shaft 40 when the probe assembly 32 is in a retracted configuration so that the probe assembly 32 does not interfere with the insertion of the distal end of the undercutting system 10 through the aperture 20 in the ilium 14.

The probe assembly 32 may have a width of between about 2 millimeters and about 5 millimeters. In certain embodiments, the probe assembly 32 may have a width of about 3 millimeters.

Side edges of the probe assembly 32 may be sufficient to cut through the tissue between the ilium 14 and the sacrum 16. Using the probe assembly 32 without the sharpened edges may reduce a tendency of the probe assembly 32 to cut into the ilium 14 and the sacrum 16 while the probe assembly 32 is rotated.

This process thereby allows an initial path between the ilium 14 and the sacrum 16 to be defined. This process is identified as defining a joint line. As is discussed in more detail below, the adjacent surfaces of the ilium 14 and the sacrum 16 may not be oriented substantially parallel to each other or substantially transverse to the orientation of the aperture 20.

When defining the joint line, the probe assembly 32 passes through the intra-articular region between the ilium 14 and the sacrum 16. The cartilage and ligaments in the intra-articular region are considerably easier to cut than the ilium 14 and the sacrum 16.

Once this path is defined, it is possible to use a cutting assembly such as is described herein to prepare a wider region between the ilium 14 and the sacrum 16 as part of the sacroiliac fusion process.

By using this process, the potential of the cutting assembly cutting too deeply into the ilium 14 or the sacrum 16 is reduced because the cutting assembly will follow the joint line that was defined by the probe assembly 32.

Alternatively, the probe assembly 32 may include a cutting surface on at least one edge thereof. In certain embodiments, cutting surfaces are provided on both side edges of the probe assembly 32. Providing the cutting surfaces on the side edges enhances the ability of the probe assembly 32 to cut while being rotated in clockwise and counter clockwise directions.

In certain embodiments, a distal end of the probe assembly 32 may not have a cutting surface. Forming the distal end without the cutting surface reduces a tendency of the probe assembly 32 to cut into the ilium 14 or the sacrum 16 as the probe assembly 32 is extended from the insertion apparatus 30.

An aperture 94 may be formed in the proximal end of the probe assembly 32. The aperture 94 may have a diameter that is slightly larger than a diameter of the attachment pin 92. Using such a configuration, the attachment pin 92 may extend into the aperture 94 to retain the probe assembly 32 in a fixed relationship with respect to the second attachment section 64.

The aperture 94 should not be too large such that the aperture 94 weakens the cutting assembly 32, which could cause the probe assembly 32 to fail when a force is applied to the probe assembly 32 such as occurs during the use of the undercutting system to cut tissue from between the ilium 14 and the sacrum 16.

The aperture 94 may be generally circular and may have a diameter of between about 0.5 millimeters and about 5 millimeters. In other embodiments, the aperture 94 may have a diameter of between about 1.5 millimeters and about 2 millimeters.

A person of skill in the art will appreciate that it is possible to attach the second attachment section 64 and the probe assembly 32 using different structures, which enable sliding and rotating of the second attachment section 64 and the probe assembly 32 with respect to the elongated shaft 40.

The probe assembly 32 having the preceding shape and characteristics may be formed from a variety of materials. A person of skill in the art will appreciate that the material used to fabricate the probe assembly 32 should be suitable for use within a human body. An example of one such material for fabricating the probe assembly 32 is nitinol. A beneficial quality of nitinol is that nitinol is bendable but returns to the unbent configuration when the force that caused the bending is removed.

Figure 9:
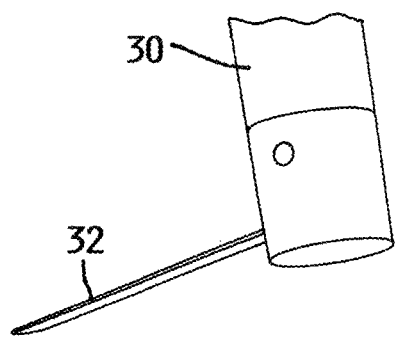
FIG. 9 is a side view of the probe assembly of FIGS. 6-8 extending from a distal end of the insertion apparatus.

The probe assembly 32 is extended from the distal end of the insertion apparatus 30, as illustrated in FIG. 9. The insertion apparatus 30 is then rotated to cause the probe assembly 32 to be move through the tissue between the ilium 14 and the sacrum 16. Rotation of the insertion apparatus 30 may be in a single direction or may alternatively be in clockwise and counterclockwise directions. This rotation may be continued until minimal resistance is felt during the rotation of the insertion apparatus 30.

Figure 6:
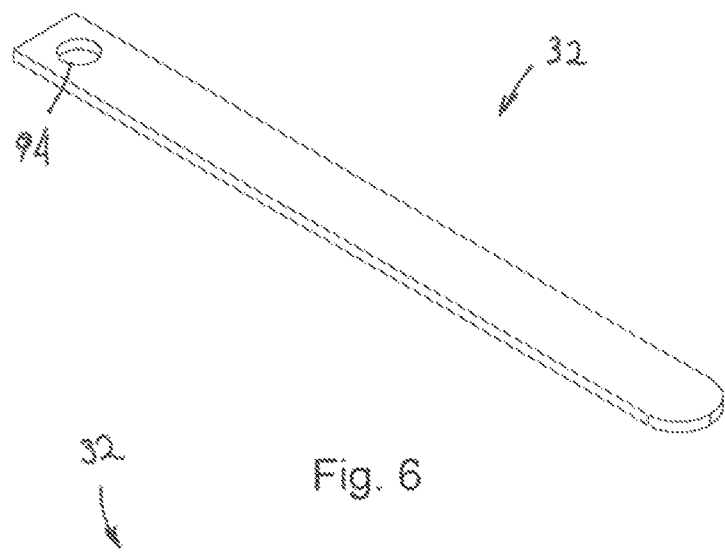
FIG. 6 is a perspective view of an end portion of a probe assembly for use with the undercutting system.
Figure 7:
FIG. 7 is a top view of the end portion of the probe assembly of FIG. 6.
Figure 8:
FIG. 8 is a side view of the end portion of the probe assembly of FIG. 6.
Figure 10:
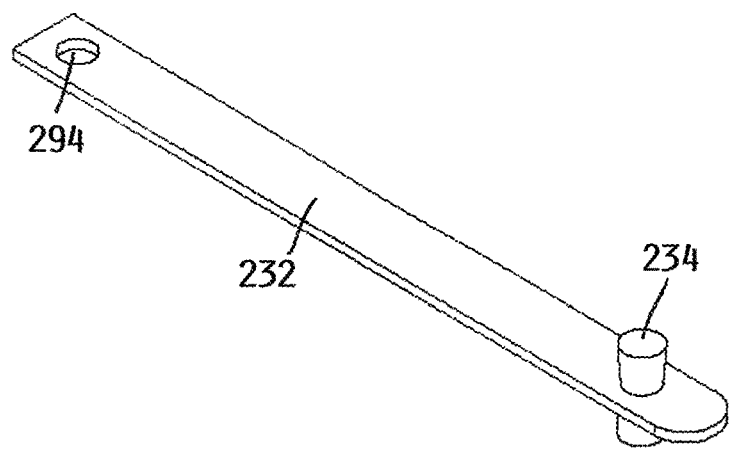
FIG. 10 is a perspective view of an end portion of an alternative probe assembly for use with the undercutting system.
Figure 11:
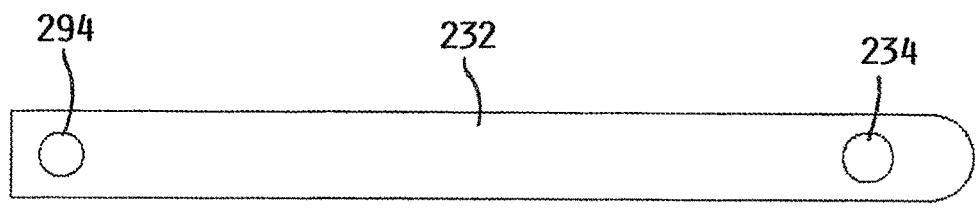
FIG. 11 is a top view of the end portion of the probe assembly of FIG. 10.
Figure 12:
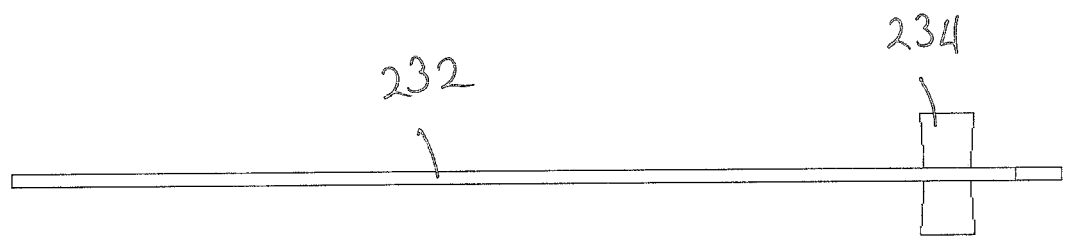
FIG. 12 is a side view of the end portion of the probe assembly of FIG. 10.

In another embodiment, a cutting element 234 may be attached proximate a distal end of the probe assembly 32, which is illustrated in FIGS. 6-8, to form a cutting assembly 232, as illustrated in FIGS. 10-12.

The cutting assembly 232 may have a thickness of up to about 2 millimeters. In certain embodiments, the cutting assembly 232 may have a thickness of between about 0.4 millimeters and about 0.6 millimeters. Using the cutting assembly 232 with the preceding dimensions provides the cutting assembly 232 with flexibility in a distal-proximal direction while resisting twisting or otherwise deforming.

The resistance enables the cutting assembly 232 to deflect in response to changes in the shape or orientation of the ilium 14 or the sacrum 16. Such deflection is important because it is much more difficult to cut through the bone of the ilium 14 and the sacrum 16 than the cartilage that is between the ilium 14 and the sacrum 16.

The configuration of the cutting assembly 232 provides the cutting assembly 232 with sufficient rigidity in a radial direction. Such a configuration allows the cutting assembly 232 to resist deformation in response to rotation of the undercutting system 10 during the cutting process such as when the tissue between the ilium 14 and the sacrum 16 is contacted with the cutting assembly 232.

The cutting assembly 232 may have a width that is no greater than an inner diameter of the elongated shaft 40. Forming the cutting assembly 232 with such a configuration enables the cutting assembly 232 to be positioned substantially within a profile of the elongated shaft 40 when the cutting assembly 232 is in a retracted configuration so that the cutting assembly 232 does not interfere with the insertion of the distal end of the undercutting system 10 extending through the aperture 20 in the ilium 14.

The cutting assembly 232 may have a width of between about 2 millimeters and about 5 millimeters. In certain embodiments, the cutting assembly 232 may have a width of about 3 millimeters.

Side edges of the cutting assembly 232 may be sufficient to cut through the tissue between the ilium 14 and the sacrum 16. Using the cutting assembly 232 without the sharpened edges may reduce a tendency of the cutting assembly 232 to cut into the ilium 14 and the sacrum 16 while the cutting assembly 232 is rotated.

Alternatively, the cutting assembly 232 may include a cutting surface on at least one edge thereof. In certain embodiments, cutting surfaces are provided on both side edges of the cutting assembly 232. Providing the cutting surfaces on the side edges enhances the ability of the cutting assembly 232 to cut while being rotated in clockwise and counter clockwise directions.

In certain embodiments, a distal end of the cutting assembly 232 may not have a cutting surface. Forming the distal end without the cutting surface reduces a tendency of the cutting assembly 232 to cut into the ilium 14 or the sacrum 16 as the cutting assembly 232 is advanced from the insertion apparatus 30.

An aperture 294 may be formed in the proximal end of the cutting assembly 232. The aperture 294 may have a diameter that is slightly larger than a diameter of the attachment pin 92. Using such a configuration, the attachment pin 92 may extend into the aperture 294 to retain the cutting assembly 232 in a fixed relationship with respect to the second attachment section 64.

The aperture 294 should not be too large such that the aperture 294 weakens the cutting assembly 232, which could cause the cutting assembly 232 to fail when a force is applied to the cutting assembly 232 such as occurs during the use of the undercutting system to cut tissue from between the ilium 14 and the sacrum 16.

The aperture 294 may be generally circular and may have a diameter of between about 0.5 millimeters and about 5 millimeters. In other embodiments, the aperture 294 may have a diameter of between about 1.5 millimeters and about 2 millimeters.

A person of skill in the art will appreciate that it is possible to attach the second attachment section 64 and the cutting assembly 232 using different structures, which enable sliding and rotating of the second attachment section 64 and the cutting assembly 232 with respect to the elongated shaft 40.

The cutting assembly 232 having the preceding shape and characteristics may be formed from a variety of materials. A person of skill in the art will appreciate that the material used to fabricate the cutting assembly 232 should be suitable for use within a human body. An example of one such material for fabricating the cutting assembly 232 is nitinol. A beneficial quality of nitinol is that nitinol is bendable but returns to the unbent configuration when the force that caused the bending is removed.

In certain embodiments, the cutting element 234 may have a generally cylindrical configuration that extends from at least one side of the cutting assembly 232. The cutting element 234 may extend in substantially equal distances on opposite sides of the cutting assembly 232.

A distance between the distal surfaces of the cutting element 234 may be limited by the inner diameter of the elongated shaft 40 so that the cutting assembly 232 with the cutting element 234 attached thereto may be retracted within the insertion apparatus 30 when the insertion apparatus 30 is inserted into and removed from the region between the ilium 14 and the sacrum 16.

In certain embodiments, a height of the cutting element 234 on opposite sides of the cutting assembly 232 is between about 1 millimeter and about 5 millimeters. In other embodiments, the height of the cutting element 234 on opposite sides of the cutting assembly 232 is about 2 millimeters.

While it is illustrated that the height of the cutting element 234 is approximately equal on opposite sides of the cutting assembly 232, it is possible to configure the cutting element so that the height of the cutting element 234 on opposite sides of the cutting assembly 232 is not approximately equal.

In certain embodiments, a diameter of the cutting element 234 may be between about 1 millimeter and about 5 millimeters. In other embodiments, the diameter of the cutting element 234 may be about 3 millimeters.

While it is illustrated that the diameter of the cutting element 234 is approximately equal on opposite sides of the cutting assembly 232, it is possible to configure the cutting element so that the diameter of the cutting element 234 on opposite sides of the cutting assembly 232 is not approximately equal.

An edge 136 of the cutting element 234 proximate the distal ends thereof may be sufficient to cut through the tissue between the ilium 14 and the sacrum 16. Using the cutting element 234 without the sharpened edges may reduce a tendency of the cutting element 234 to cut into the ilium 14 and the sacrum 16 while the cutting assembly 232 is rotated. In other embodiments, the cutting element 234 may have a diameter proximate the cutting assembly 232 that is less than a diameter distal the cutting assembly 232.

Alternatively, the edge 236 of the cutting element 234 proximate the distal ends thereof may be sharpened to facilitate cutting of tissue proximate the surfaces of the ilium 14 and the sacrum 16.

A distance between the distal ends of the cutting element 234 thereby defines a thickness of a region between the ilium 14 and the sacrum 16 that is prepared with the undercutting system 10.

The undercutting system 10 may include a plurality of cutting assemblies 232 having cutting elements 234 with different distances between the distal ends thereof. One of the cutting assemblies 232 having the cutting element 234 with the smallest distance between the distal ends may be initially used. Thereafter, cutting assemblies 232 having the cutting elements 234 with progressively longer distances between the distal ends may be used to form a progressively wider region between the ilium 14 and the sacrum 16.

While it is desirable to prepare the surfaces of the ilium 14 and the sacrum 16 by exposing bleeding bone, it is desirable to avoid the cutting assembly 232 and the cutting element 234 digging into the surface of the ilium 14 or the sacrum 16 too deeply. When the cutting assembly 232 digs too deeply into the surface of the ilium 14 or the sacrum 16, it becomes more difficult to rotate the cutting assembly 232 because the ilium 14 and the sacrum 16 are much harder than the tissue located between the ilium 14 and the sacrum 16. The cutting assembly 232 and the cutting element 234 having the characteristics set forth above meet these criteria.

The cutting element 234 having the preceding shape and characteristics may be formed from a variety of materials. A person of skill in the art will appreciate that the material used to fabricate the cutting element 234 should be suitable for use within a human body. An example of one such suitable material for fabricating the cutting element 234 is stainless steel.

The cutting element 234 may be attached to the cutting assembly 232 using a variety of techniques that cause the cutting element 234 to be fixedly attached to the cutting assembly 232. One such suitable technique for attaching the cutting element 234 to the cutting assembly 232 is welding.

Alternatively, it is possible to fabricate the cutting assembly 232 and the cutting element 234 as a single unit such as by machining a block to provide the substantially flat cutting assembly 232 and the cutting element 234 that extends from the cutting assembly 232.

Figure 13:
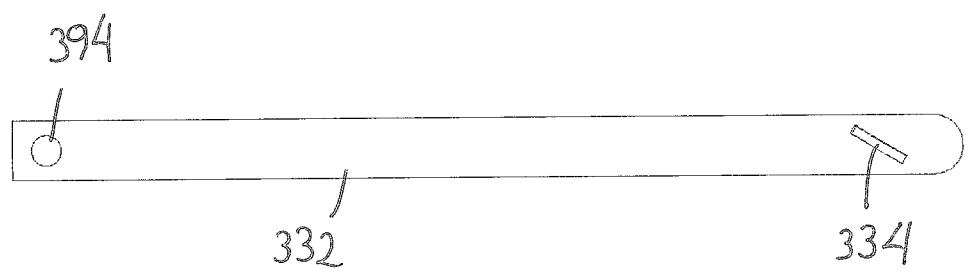
FIG. 13 is a top view of an end portion of another probe assembly for use with the undercutting system.
Figure 14:
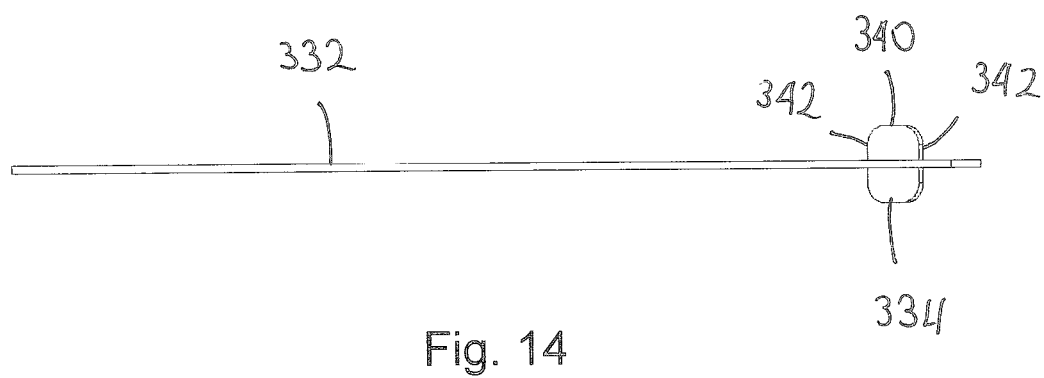
FIG. 14 is a side view of the end portion of the probe assembly of FIG. 13.

In another embodiment, a cutting element 334 may be attached proximate a distal end of the probe assembly 32, which is illustrated in FIGS. 6-8, to form a cutting assembly 332, as illustrated in FIGS. 13 and 14.

The cutting assembly 332 may have a thickness of up to about 2 millimeters. In certain embodiments, the cutting assembly 332 may have a thickness of between about 0.4 millimeters and about 0.6 millimeters. Using the cutting assembly 332 with the preceding dimensions provides the cutting assembly 332 with flexibility in a distal-proximal direction while resisting twisting or otherwise deforming.

The resistance enables the cutting assembly 332 to deflect in response to changes in the shape or orientation of the ilium 14 or the sacrum 16. Such deflection is important because it is much more difficult to cut through the bone of the ilium 14 and the sacrum 16 than the tissue that is between the ilium 14 and the sacrum 16.

The configuration of the cutting assembly 332 provides the cutting assembly 332 with sufficient rigidity in a radial direction. Such a configuration allows the cutting assembly 332 to resist deformation in response to rotation of the undercutting system 10 during the cutting process such as when the tissue between the ilium 14 and the sacrum 16 is contacted with the cutting assembly 332.

The cutting assembly 332 may have a width that is no greater than an inner diameter of the elongated shaft 40. Forming the cutting assembly 332 with such a configuration enables the cutting assembly 332 to be positioned substantially within a profile of the elongated shaft 40 when the cutting assembly 332 is in a retracted configuration so that the cutting assembly 332 does not interfere with the insertion of the distal end of the undercutting system 10 extending through the aperture 20 in the ilium 14.

The cutting assembly 332 may have a width of between about 2 millimeters and about 5 millimeters. In certain embodiments, the cutting assembly 332 may have a width of about 3 millimeters.

Side edges of the cutting assembly 332 may be sufficient to cut through the tissue between the ilium 14 and the sacrum 16. Using the cutting assembly 332 without the sharpened edges may reduce a tendency of the cutting assembly 332 to cut into the ilium 14 and the sacrum 16 while the cutting assembly 332 is rotated to cut the tissue that is between the ilium 14 and the sacrum 16.

Alternatively, the cutting assembly 332 may include a cutting surface on at least one edge thereof. In certain embodiments, cutting surfaces are provided on both side edges of the cutting assembly 332. Providing the cutting surfaces on the side edges enhances the ability of the cutting assembly 332 to cut while being rotated in clockwise and counter clockwise directions.

In certain embodiments, a distal end of the cutting assembly 332 may not have a cutting surface. Forming the distal end without the cutting surface reduces a tendency of the cutting assembly 332 to cut into the ilium 14 or the sacrum 16 as the cutting assembly 332 is advanced from the insertion apparatus 30.

An aperture 394 may be formed in the proximal end of the cutting assembly 332. The aperture 394 may have a diameter that is slightly larger than a diameter of the attachment pin 92. Using such a configuration, the attachment pin 92 may extend into the aperture 394 to retain the cutting assembly 332 in a fixed relationship with respect to the second attachment section 64.

The aperture 394 should not be too large such that the aperture 394 weakens the cutting assembly 332, which could cause the cutting assembly 332 to fail when a force is applied to the cutting assembly 332 such as occurs during the use of the undercutting system to cut tissue from between the ilium 14 and the sacrum 16.

The aperture 394 may be generally circular and may have a diameter of between about 0.5 millimeters and about 5 millimeters. In other embodiments, the aperture 394 may have a diameter of between about 1.5 millimeters and about 2 millimeters.

A person of skill in the art will appreciate that it is possible to attach the second attachment section 64 and the cutting assembly 332 using different structures, which enable sliding and rotating of the second attachment section 64 and the cutting assembly 332 with respect to the elongated shaft 40.

The cutting assembly 332 having the preceding shape and characteristics may be formed from a variety of materials. A person of skill in the art will appreciate that the material used to fabricate the cutting assembly 332 should be suitable for use within a human body. An example of one such material for fabricating the cutting assembly 332 is nitinol. A beneficial quality of nitinol is that nitinol is bendable but returns to the unbent configuration when the force that caused the bending is removed.

In certain embodiments, the cutting element 334 may have a generally planar configuration that extends from at least one side of the cutting assembly 332. The cutting element 334 may extend in substantially equal distances on opposite sides of the cutting assembly 332. The cutting element 334 may have a generally rectangular shape that is defined by a distal edge 340 and a pair of side edges 342.

While it is illustrated that a height of the cutting element 334 is approximately equal on opposite sides of the cutting assembly 332, it is possible to configure the cutting element 334 so that the height of the cutting element 334 is not approximately equal on opposite sides of the cutting assembly 332.

The height of the distal edge 340 may be limited by the inner diameter of the elongated shaft 40 so that the cutting assembly 332 may be retracted within the insertion apparatus 30 when the insertion apparatus 30 is inserted into and removed from the region between the ilium 14 and the sacrum 16.

In certain embodiments, the height of the cutting element 334 on opposite sides of the cutting assembly 332 is between about 1 millimeter and about 5 millimeters. In other embodiments, the height of the cutting element 334 on opposite sides of the cutting assembly 332 is about 3 millimeters.

In certain embodiments, a width of the cutting element 334 is approximately the same on opposite sides of the cutting assembly 332. The width of the cutting element 334 may be between about 1 millimeter and about 5 millimeters. In other embodiments, the width of the cutting element 334 is about 3 millimeters.

Corners proximate the intersection of the distal edge 340 and each of the side edges 342 may be curved. While such curvature could reduce the cutting ability of the cutting element 334 that could be attained if the distal edge 340 and the side edge 342 intersected at a corner, this curvature may reduce the tendency of the cutting element 334 to dig too deeply into the surfaces of the ilium 14 and the sacrum 16. As a result of this configuration, the cutting element 334 would preferentially cut into the tissue between the ilium 14 and the sacrum 16 as opposed to cutting the ilium 14 and the sacrum 16.

While it is illustrated that the cutting element 334 has a substantially equal thickness, it is possible for the thickness of the cutting element 334 to vary. In certain embodiments, the thickness of the cutting element 334 may be greater proximate to the cutting assembly 332 to resist bending or deformation of the cutting element 334.

In certain embodiments, a thickness of the cutting element 334 may be between about 0.2 millimeters and about 2 millimeters. In other embodiments, the thickness of the cutting element 334 may be about 0.5 millimeters.

While it is illustrated that the thickness of the cutting element 334 is approximately equal on opposite sides of the cutting assembly 332, it is possible to configure the cutting element 334 so that the thickness of the cutting element 334 on opposite sides of the cutting assembly 332 is not approximately equal.

The edge 340 of the cutting element 334 proximate the distal ends thereof may be sufficient to cut through the tissue between the ilium 14 and the sacrum 16. Using the cutting element 334 without the sharpened edges may reduce a tendency of the cutting element 334 to cut into the ilium 14 and the sacrum 16 while the cutting assembly 332 is rotated.

Alternatively, the edge 236 of the cutting element 334 proximate the distal ends thereof may be sharpened to facilitate cutting of tissue proximate the surfaces of the ilium 14 and the sacrum 16.

The cutting element 334 may be oriented at an angle with respect to the cutting assembly 332 so that the cutting element 334 is not generally parallel to the length of the cutting assembly 332. In certain embodiments, the cutting element 334 may be oriented at an angle of between about 0 degrees and about 60 degrees. In other embodiments, the angle between the cutting element 334 and the cutting assembly 332 may be about 30 degrees.

Orienting the cutting element 334 at the angle with respect to the length of the cutting assembly 332 causes one of the edges to be disposed forwardly. Such a configuration may increase the ability of the cutting element 334 to cut tissue from between the ilium 14 and the sacrum 16 as the cutting element 334 is rotated.

While it is illustrated that the cutting element 334 is oriented generally transverse to the surface of the cutting assembly 332, it is possible for the cutting element 334 to be oriented at an angle with respect to the surface of the cutting assembly 332. In certain embodiments, the angle between the cutting element 334 and the surface of the cutting assembly 332 may be between about 60 degrees and about 90 degrees.

While it is possible for the cutting element 334 to be placed at the distal end of the cutting assembly 332, in certain embodiments, the cutting element 334 is mounted a distance from the distal end of the cutting assembly 332. Mounting the cutting element 334 a distance from the distal end of the cutting assembly 332 enables the cutting assembly 332 to define a path through the tissue between the ilium 14 and the sacrum 16, as opposed to the cutting element 334 being the primary component that defines the path through the tissue between the ilium 14 and the sacrum 16.

A distance between the cutting element 334 and the distal end of the cutting assembly 332 may be between about 1 millimeter and about 5 millimeters. In other embodiments, the distance between the cutting element 334 and the distal end of the cutting assembly 332 may be about 3 millimeters.

The cutting element 334 may be positioned at a location that is approximately intermediate between the side edges of the cutting assembly 332. Placing the cutting element 334 in this location may reduce twisting of the cutting assembly 332, which could potentially occur if the cutting element 334 was located closer to one of the side edges of the cutting assembly 332.

The cutting element 334 having the preceding shape and characteristics may be formed from a variety of materials. A person of skill in the art will appreciate that the material used to fabricate the cutting element 334 should be suitable for use within a human body. An example of one such material for fabricating the cutting element 334 is nitinol.

In certain embodiments, the cutting assembly 332 may be fabricated separately from the cutting element 334. Forming the structure in this manner enables different materials to be used for fabricating the cutting assembly 332 and the cutting element 334 so that the respective materials may be optimized based upon the function of the associated structure.

The cutting element 334 may be attached to the cutting assembly 332 using a variety of techniques that cause the cutting element 334 to be fixedly attached to the cutting assembly 332. One such suitable technique for attaching the cutting element 334 to the cutting assembly 332 is welding.

Alternatively, it is possible to fabricate the cutting assembly 332 and the cutting element 334 as a single unit such as by machining a block to provide a substantially flat cutting assembly 332 and a cutting element 334 that extends from the cutting assembly 332.

The undercutting system 10 may include a plurality of cutting assemblies 332 with cutting elements 334 having different distances between the distal ends thereof. One of the cutting assemblies 332 with the cutting element 334 having the smallest distance between the distal ends thereof may be initially used. Thereafter, cutting assemblies 332 with cutting element 334 having progressively longer distances between the distal ends thereof may be used to form a progressively wider region between the ilium and the sacrum.

Placing the cutting element 334 on the relatively flexible cutting assembly 332 enables the region between the ilium 14 and the sacrum 16 to be prepared for the sacroiliac fusion while minimizing the cutting assembly 332 digging into the surface of the ilium 14 or the sacrum 16.

While it is desirable to prepare the surfaces of the ilium 14 and the sacrum 16 by exposing bleeding bone, it is desirable to avoid the cutting assembly 332 digging into the surface of the ilium 14 or the sacrum 16 too deeply. When the cutting assembly 332 digs too deeply into the surface of the ilium 14 or the sacrum 16, it becomes more difficult to rotate the cutting assembly 332 because the ilium 14 and the sacrum 16 are much harder than the tissue located between the ilium 14 and the sacrum 16. The cutting assembly 332 and the cutting element 334 having the characteristics set forth above meet these criteria.

Figure 15:
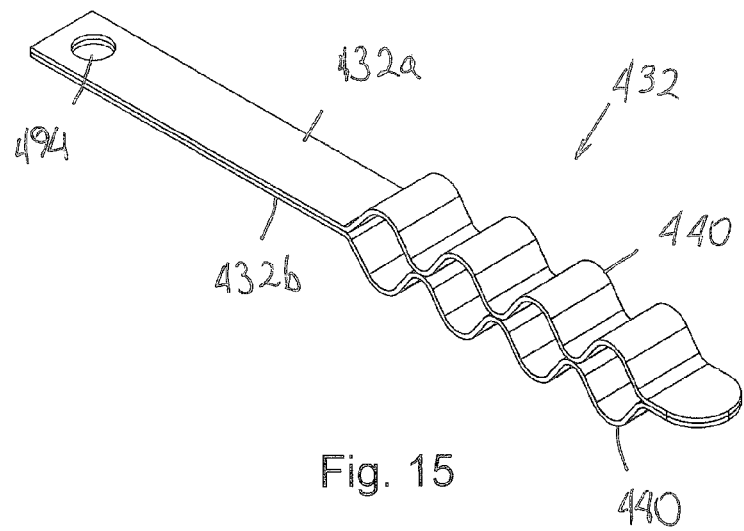
FIG. 15 is a perspective view of an undercutting system for use in a sacroiliac fusion procedure.
Figure 16:
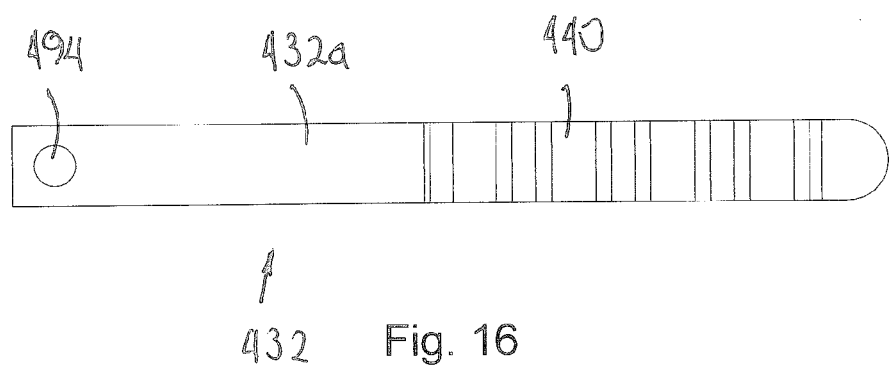
FIG. 16 is a top view of the end portion of the probe assembly of FIG. 15.
Figure 17:
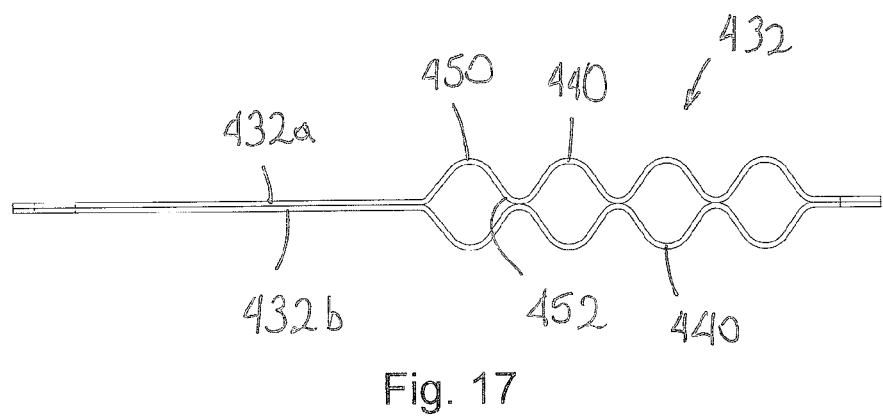
FIG. 17 is a side view of the end portion of the probe assembly of FIG. 15.

In another embodiment, the cutting assembly 432 may have an initial elongated shape that is generally similar to the shape of the probe assembly 32 illustrated in FIGS. 6-8. However, the cutting assembly 432 may include two cutting assembly strips 432a, 432b that each have a plurality of waves 440 formed therein, as illustrated in FIGS. 15-17.

The cutting assembly strips 432a, 432b may have a thickness of up to about 2 millimeters. In certain embodiments, the cutting assembly strips 432a, 432b may have a thickness of between about 0.1 millimeters and about 0.3 millimeters. Using the cutting assembly strips 432a, 432b with the preceding dimensions provides the cutting assembly strips 432a, 432b with flexibility in a distal-proximal direction while resisting twisting or otherwise deforming.

The resistance enables the cutting assembly strips 432a, 432b to deflect in response to changes in the shape or orientation of the ilium 14 or the sacrum 16. Such deflection is important because it is much more difficult to cut through the bone of the ilium 14 and the sacrum 16 than the tissue that is between the ilium 14 and the sacrum 16.

The configuration of the cutting assembly strips 432a, 432b provides the cutting assembly strips 432a, 432b with sufficient rigidity in a radial direction. Such a configuration allows the cutting assembly strips 432a, 432b to resist deformation in response to rotation of the undercutting system during the cutting process such as when the tissue between the ilium 14 and the sacrum 16 is contacted with the cutting assembly 432.

The cutting assembly strips 432a, 432b may have a width that is no greater than an inner diameter of the elongated shaft 40. Forming the cutting assembly strips 432a, 432b with such a configuration enables the cutting assembly 432 to be positioned substantially within a profile of the elongated shaft 40 when the cutting assembly 432 is in a retracted configuration so that the cutting assembly 432 does not interfere with the insertion of the distal end of the undercutting system extending through the aperture 20 in the ilium 14.

The cutting assembly strips 432a, 432b may have a width of between about 2 millimeters and about 5 millimeters. In certain embodiments, the cutting assembly strips 432a, 432b may have a width of about 3 millimeters.

Side edges of the cutting assembly strips 432a, 432b may be sufficient to cut through the tissue between the ilium 14 and the sacrum 16. Using the cutting assembly strips 432a, 432b without the sharpened edges may reduce a tendency of the cutting assembly 432 to cut into the ilium 14 and the sacrum 16 while the cutting assembly 432 is rotated.

Alternatively, the cutting assembly strips 432a, 432b may include a cutting surface on at least one edge thereof. In certain embodiments, cutting surfaces are provided on both side edges of the cutting assembly strips 432a, 432b. Providing the cutting surfaces on the side edges enhances the ability of the cutting assembly 432 to cut the tissue between the ilium 14 and the sacrum 16 while the cutting assembly 432 is rotated in clockwise and counter clockwise directions.

In certain embodiments, a distal end of the cutting assembly strips 432a, 432b may not have a cutting surface. Forming the distal end without the cutting surface reduces a tendency of the cutting assembly 432 to cut into the ilium 14 or the sacrum 16 as the cutting assembly 432 is advanced from the insertion apparatus 30.

An aperture 494 may be formed in the proximal end of the cutting assembly 432. The aperture 494 may have a diameter that is slightly larger than a diameter of the attachment pin 92. Using such a configuration, the attachment pin 92 may extend into the aperture 494 to retain the cutting assembly 432 in a fixed relationship with respect to the second attachment section 64.

The aperture 494 should not be too large such that the aperture 494 weakens the cutting assembly 432, which could cause the cutting assembly 432 to fail when a force is applied to the cutting assembly 432 such as occurs during the use of the undercutting system to cut tissue from between the ilium 14 and the sacrum 16.

The aperture 494 may be generally circular and may have a diameter of between about 0.5 millimeters and about 5 millimeters. In other embodiments, the aperture 494 may have a diameter of between about 1.5 millimeters and about 2 millimeters.

A person of skill in the art will appreciate that it is possible to attach the second attachment section 64 and the cutting assembly 432 using different structures, which enable sliding and rotating of the second attachment section 64 and the cutting assembly 432 with respect to the elongated shaft 40.

In one configuration, each of the cutting assembly strips 432a, 432b is formed into the wavy configuration and then the cutting assembly strips 432a, 432b are attached to each other. The wave section 440 may be positioned proximate the distal end of the cutting assembly strips 432a, 432b.

In certain embodiments, the wave section 440 is located on between about 30 percent and about 70 percent of the length of the cutting assembly strips 432a, 432b. In other embodiments, the wave section 440 is located on between about 50 and 60 percent of the length of the cutting assembly strips 432a, 432b.

The length of the wave section 440 on the cutting assembly strips 432a, 432b may be between about 10 millimeters and about 30 millimeters. In certain embodiments, the length of the wave section 440 on the cutting assembly strips 432a, 432b may be between about 15 millimeters and about 20 millimeters.

There may be a spacing between the distal most wave and the distal end of the cutting assembly strip 432a, 432b. Forming the cutting assembly strips 432a, 432b with this configuration provides the cutting assembly 432 with a relatively flat distal end. This relatively flat distal end may be used for guiding the cutting assembly 432 through the tissue between the ilium 14 and the sacrum 16, as opposed to allowing the cutting assembly 432 to cut into the surface of the ilium 14 or the sacrum 16.

In certain embodiments, a spacing between the distal most wave and the distal end of the cutting assembly strips 432a, 432b is between about 1 millimeter and about 5 millimeters. In other embodiments, the spacing between the distal most wave and the distal end of the cutting assembly strips 432a, 432b is between about 2 millimeters and about 3 millimeters.

The number of waves 440 included on the cutting assembly strips 432a, 432b may be determined by a variety of factors. Examples of these factors include the angle at which the cutting assembly strips 432a, 432b may be bent without significantly impacting the strength of the cutting assembly strips 432a, 432b and without causing a sharp bend line to be formed between the ascending and descending portions of the cutting assembly strips 432a, 432b.

In certain embodiments, there are between 2 and 10 waves 440 formed in the cutting assembly strips 432a, 432b. In other embodiments, there are about four waves 440 formed in the cutting assembly strips 432a, 432b. While it is illustrated that each of the waves 440 has a substantially similar shape, it is possible to form the waves 440 having different shapes. For example, the waves 440 may have differing heights and differing widths.

To increase the amount of tissue between the ilium 14 and the sacrum 16 that can be cut using the cutting assembly 432, it may be desirable for the waves 440 on the two adjacent cutting assembly strips 432a, 432b to have a height that is close to the distance between the ilium 14 and the sacrum 16. Since the distance between the ilium 14 and the sacrum 16 may vary at different locations in the sacroiliac joint, the height of the waves 440 may be selected based upon the minimum distance between the ilium 14 and the sacrum 16.

Since there are two cutting assembly strips 432a, 432b used for fabricating the cutting assembly 432, the waves 440 on each of the cutting assembly strips 432a, 432b may have a maximum height that is less than about one-half of a distance between the surfaces of the ilium 14 and the sacrum 16. Forming the waves 440 with the preceding maximum height minimizes the potential that the upper portion 450 of the waves 440 will be forced into the surface of the ilium 14 or the sacrum 16.

Since the ilium 14 and the sacrum 16 are formed from a material that is harder than the tissue between the ilium 14 and the sacrum 16, forcing the upper portion 450 of the waves 440 into the surface of the ilium 14 or the sacrum 16 will make it harder to operate the undercutting system.

In certain embodiments, a distance between the upper portion 450 and the lower portion 452 of the waves 440 on each of the cutting assembly strips 432a, 432b will be between about 1 millimeter and about 3 millimeters. In other embodiments, the distance between the upper portion 450 and the lower portion 452 of the waves 440 on each of the cutting assembly strips 432a, 432b may be about 1.75 millimeters.

A distance between the upper portions 450 of adjacent waves 440 may be between about 2 millimeters and about 6 millimeters. In certain embodiments, the distance between the upper portions 450 of adjacent waves 440 may be about 4 millimeters.

While it is possible for the radius of curvature of the upper portions 450 and the lower portions 452 of the waves to be substantially equal to each other, in certain embodiments, the radius of curvature of the upper portions 450 of the waves 440 is greater than the radius of curvature of the lower portions 452 of the waves 440.

Forming the waves 440 with the radius of curvature of the upper portions 450 being greater than the radius of curvature of the lower portions 452 provides the upper portions 450 with a greater length than the lower portions 452. This configuration increases the ability of the cutting assembly 432 to cut tissue located between the ilium 14 and the sacrum 16.

The radius of curvature of the upper portions 450 of the waves 440 may be between about 0.30 millimeters and about 2 millimeters. In certain embodiments, the radius of curvature of the upper portions 450 of the waves 440 is between about 0.80 millimeters and about 0.90 millimeters.

The radius of curvature of the lower portions 452 of the waves 440 may be between about 0.30 millimeters and about 2 millimeters. In certain embodiments, the radius of curvature of the lower portions 452 of the waves 440 is between about 0.50 millimeters and about 0.60 millimeters.

The waves 440 may be offset from the proximal end of the cutting assembly strips 432a, 432b so that the proximal ends of two cutting assembly strips 432a, 432b may be placed adjacent to each other while the lower portions 452 of the waves 440 on the adjacent cutting assembly strips 432a, 432b are adjacent to each other.

In certain embodiments, the offset from the proximal end and the center of the waves 440 that is intermediate the upper portion 450 and the lower portion 452 is between about 0.40 millimeters and about 2 millimeters. In other embodiments, the offset from the proximal end and the center of the waves 440 that is intermediate the upper portion 450 and the lower portion 452 is between about 0.60 millimeters and about 0.90 millimeters.

Similarly, the waves 440 may be offset from the distal end of the cutting assembly strip 432a, 432b so that the distal ends of two cutting assembly strips 432a, 432b may be placed adjacent to each other while the lower portions 452 of the waves 440 on the adjacent cutting assembly strips 432a, 432b are adjacent to each other.

In certain embodiments, the offset from the distal end and the center of the waves 440 that is intermediate the upper portion 450 and the lower portion 452 is between about 0.40 millimeters and about 2 millimeters. In other embodiments, the offset from the distal end and the center of the waves 440 that is intermediate the upper portion 450 and the lower portion 452 is between about 0.60 millimeters and about 0.90 millimeters.

The two cutting assembly strips 432a, 432b may be attached to each other proximate the distal ends thereof. One suitable technique that may be used for attaching the distal ends of the cutting assembly strips 432a, 432b to each other is by welding. Laser welding is an example of one suitable welding technique.

Since the proximal ends of the cutting assembly strips 432a, 432b are attached to the other portions of the undercutting system, it may not be necessary to attach the proximal ends of the cutting assembly strips 432a, 432b to each other. Similarly, it may not be necessary to fasten the cutting assembly strips 432a, 432b to each other proximate the lower portions 452 of the waves 440. Not attaching the proximal ends of the cutting assembly strips 432a, 432b and the lower portions 452 of the waves 440 may increase the flexibility of the cutting assembly 432.

While it is possible to sharpen at least a portion of the side edges of the cutting assembly strips 432a, 432b to increase the ability of the cutting assembly 432 to cut the tissue between the ilium 14 and the sacrum 16, the cutting assembly 432 may be fabricated without sharpening the side edges of the cutting assembly strips 432a, 432b.

Even without sharpening, the side edges of the cutting assembly strips 432a, 432b may be sufficiently sharp to cut the tissue between the ilium 14 and the sacrum 16. If the side edges of the cutting assembly strips 432a, 432b are sharpened, the side edges may be too sharp, which could make it more likely that the cutting assembly 432 would cut into the ilium 14 and the sacrum 16.

Even though it is desired to prepare the surfaces of the ilium 14 and the sacrum 16 with the undercutting system, it is generally desirable to not cut too deeply into the ilium 14 and the sacrum 16, as such cutting would not only increase the time associated with preparing the ilium 14 and the sacrum 16 for the sacroiliac fusion but could also negatively impact the strength of the ilium 14 and the sacrum 16.

The undercutting system may include a plurality of cutting assemblies 432 having waves 440 with different heights. One of the cutting assemblies 432 with having the smallest wave height may be initially used. Thereafter, cutting assemblies 432 having progressively larger wave heights may be used to form a progressively wider region between the ilium 14 and the sacrum 16.

The cutting assembly strips 432a, 432b having the preceding shape and characteristics may be formed from a variety of materials. A person of skill in the art will appreciate that the material used to fabricate the cutting assembly strips 432a, 432b should be suitable for use within a human body. An example of one such material for fabricating the cutting assembly strips 432a, 432b is nitinol. A beneficial quality of nitinol is that nitinol is bendable but returns to the unbent configuration when the force that caused the bending is removed.

Figure 18:
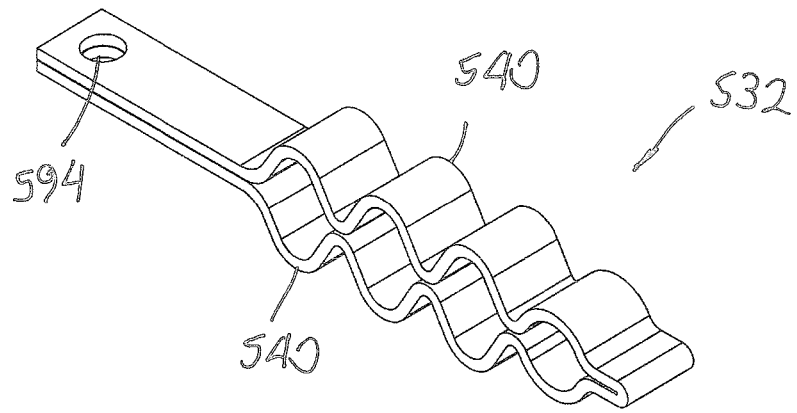
FIG. 18 is a perspective view of an undercutting system for use in a sacroiliac fusion procedure.
Figure 19:
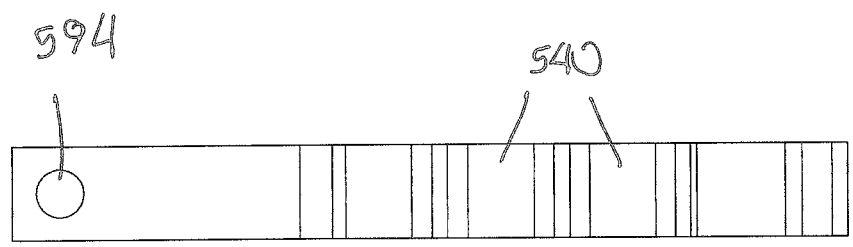
FIG. 19 is a top view of the end portion of the probe assembly of FIG. 18.
Figure 20:
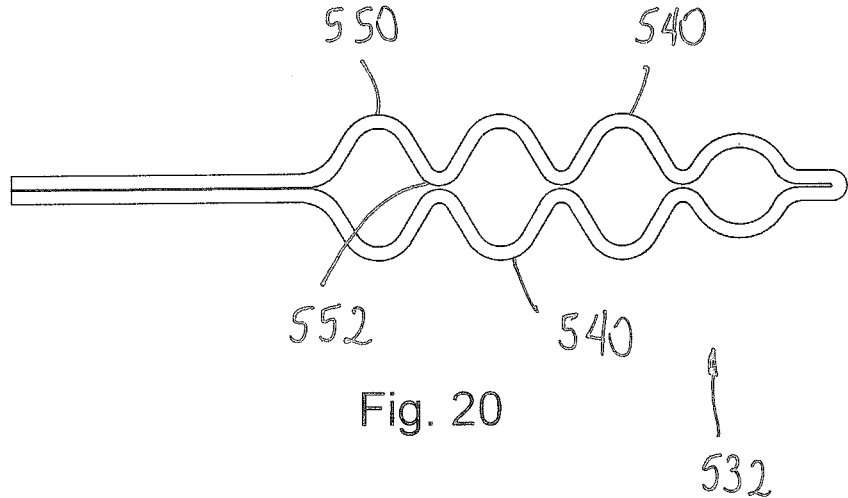
FIG. 20 is a side view of the end portion of the probe assembly of FIG. 18.
Figure 23:
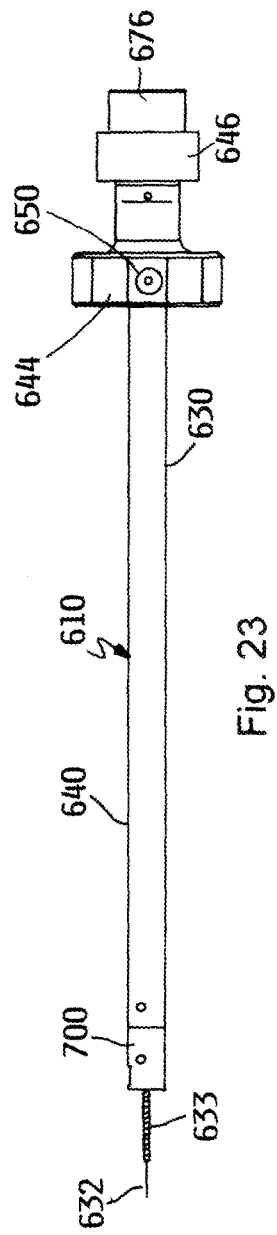
FIG. 23 is a second side view of the undercutting system of FIG. 21.

In another embodiment, the cutting assembly 532 may have a shape that is generally similar to the shape of the cutting assembly 432 illustrated in FIGS. 15-17. This cutting assembly 532 may include a single strip of material in which a plurality of waves 540 formed therein and in which the ends of the single strip of material are positioned adjacent to each other so that the single strip of material is in a looped configuration, as illustrated in FIGS. 18-20.

The cutting assembly 532 may have a thickness of up to about 2 millimeters. In certain embodiments, the cutting assembly 532 may have a thickness of between about 0.1 millimeters and about 0.3 millimeters. Using the cutting assembly 532 with the preceding dimensions provides the cutting assembly 532 with flexibility in a distal-proximal direction while resisting twisting or otherwise deforming.

The resistance enables the cutting assembly 532 to deflect in response to changes in the shape or orientation of the ilium 14 or the sacrum 16. Such deflection is important because it is much more difficult to cut through the bone of the ilium 14 and the sacrum 16 than the cartilage that is between the ilium 14 and the sacrum 16.

The configuration of the cutting assembly 532 provides the cutting assembly 532 with sufficient rigidity in a radial direction. Such a configuration allows the cutting assembly 532 to resist deformation in response to rotation of the undercutting system during the cutting process such as when the tissue between the ilium 14 and the sacrum 16 is contacted with the cutting assembly 532.

The cutting assembly 532 may have a width that is no greater than an inner diameter of the elongated shaft 40. Forming the cutting assembly 532 with such a configuration enables the cutting assembly 532 to be positioned substantially within a profile of the elongated shaft 40 when the cutting assembly 532 is in a retracted configuration so that the cutting assembly 532 does not interfere with the insertion of the distal end of the undercutting system extending through the aperture 20 in the ilium 14.

The cutting assembly 532 may have a width of between about 2 millimeters and about 5 millimeters. In certain embodiments, the cutting assembly 532 may have a width of about 3 millimeters.

Side edges of the cutting assembly 532 may be sufficient to cut through the tissue between the ilium 14 and the sacrum 16. Using the cutting assembly 532 without the sharpened edges may reduce a tendency of the cutting assembly 532 to cut into the ilium 14 and the sacrum 16 while the cutting assembly 532 is rotated.

Alternatively, the cutting assembly 532 may include a cutting surface on at least one edge thereof. In certain embodiments, cutting surfaces are provided on both side edges of the cutting assembly 532. Providing the cutting surfaces on the side edges enhances the ability of the cutting assembly 532 to cut the tissue between the ilium 14 and the sacrum 16 while the cutting assembly 532 is rotated in clockwise and counter clockwise directions.

In certain embodiments, a distal end of the cutting assembly 532 may not have a cutting surface. Forming the distal end without the cutting surface reduces a tendency of the cutting assembly 532 to cut into the ilium 14 or the sacrum 16 as the cutting assembly 532 is a from the insertion apparatus 30.

An aperture 594 may be formed in the proximal end of the cutting assembly 532. The aperture 594 may have a diameter that is slightly larger than a diameter of the attachment pin 92. Using such a configuration, the attachment pin 92 may extend into the aperture 594 to retain the cutting assembly 532 in a fixed relationship with respect to the second attachment section 64.

The aperture 594 should not be too large such that the aperture 594 weakens the cutting assembly 532, which could cause the cutting assembly 532 to fail when a force is applied to the cutting assembly 532 such as occurs during the use of the undercutting system to cut tissue from between the ilium 14 and the sacrum 16.

The aperture 594 may be generally circular and may have a diameter of between about 0.5 millimeters and about 5 millimeters. In other embodiments, the aperture 594 may have a diameter of between about 1.5 millimeters and about 2 millimeters.

A person of skill in the art will appreciate that it is possible to attach the second attachment section 64 and the cutting assembly 532 using different structures, which enable sliding and rotating of the second attachment section 64 and the cutting assembly 532 with respect to the elongated shaft 40.

In one configuration, the cutting assembly 532 is formed into the wavy configuration and then the cutting assembly 532 is bent in half. The wave section 540 may be positioned proximate the distal end of the cutting assembly 532.

In certain embodiments, the wave section 540 is located on between about 30 percent and about 70 percent of the length of the cutting assembly 532. In other embodiments, the wave section 540 is located on between about 50 and 60 percent of the length of the cutting assembly 532.

The length of the wave section 540 on the cutting assembly 532 may be between about 10 millimeters and about 30 millimeters. In certain embodiments, the length of the wave section 540 on the cutting assembly 532 may be between about 15 millimeters and about 20 millimeters.

There may be a spacing between the distal most wave and the distal end of the cutting assembly 532. Forming the cutting assembly 532 with this configuration provides the cutting assembly 532 with a relatively flat distal end. This relatively flat distal end may be used for guiding the cutting assembly 532 through the tissue between the ilium 14 and the sacrum 16, as opposed to allowing the cutting assembly 532 to cut into the surface of the ilium 14 or the sacrum 16.

In certain embodiments, a spacing between the distal most wave and the distal end of the cutting assembly 532 is between about 1 millimeter and about 5 millimeters. In other embodiments, the spacing between the distal most wave and the distal end of the cutting assembly 532 is between about 2 millimeters and about 3 millimeters.

The number of waves 540 included on the cutting assembly 532 may be determined by a variety of factors. Examples of these factors include the angle at which the cutting assembly 532 may be bent without significantly impacting the strength of the cutting assembly 532 and without causing a sharp bend line to be formed between the ascending and descending portions of the cutting assembly 532.

In certain embodiments, there are between 2 and 10 waves 540 formed on each side the cutting assembly 532. In other embodiments, there are about four waves 540 formed on each side of the cutting assembly 532. While it is illustrated that each of the waves 540 has a substantially similar shape, it is possible to formed the waves 540 having different shapes. For example, the waves 540 may have differing heights and differing widths.

To increase the amount of tissue between the ilium 14 and the sacrum 16 that can be cut using the cutting assembly 532, it may be desirable for the waves 540 on the two sides of the cutting assembly 532 to have a height that is close to the distance between the ilium 14 and the sacrum 16. Since the distance between the ilium 14 and the sacrum 16 may vary at different locations in the sacroiliac joint, the height of the waves 540 may be selected based upon the minimum distance between the ilium 14 and the sacrum 16.

Since there are two sides of the cutting assembly 532 on which the waves 540 are formed, the waves 540 on each side may have a maximum height that is less than about one-half of a distance between the surfaces of the ilium 14 and the sacrum 16. Forming the waves 540 with the preceding maximum height minimizes the potential that the upper portion 550 of the waves 540 will be forced into the surface of the ilium 14 or the sacrum 16, as the cutting assembly 532 is rotated.

Since the ilium 14 and the sacrum 16 are formed from a material that is harder than the tissue between the ilium 14 and the sacrum 16, forcing the upper portion 550 of the waves 540 into the surface of the ilium 14 or the sacrum 16 will make it harder to operate the undercutting system.

In certain embodiments, a distance between the upper portion 550 and the lower portion 552 of the waves 540 on each side of the cutting assembly 532 will be between about 1 millimeter and about 3 millimeters. In other embodiments, the distance between the upper portion 550 and the lower portion 552 of the waves 540 on each side of the cutting assembly 532 may be about 1.75 millimeters.

A distance between the upper portions 550 of adjacent waves 540 may be between about 2 millimeters and about 6 millimeters. In certain embodiments, the distance between the upper portions 550 of adjacent waves 540 may be about 4 millimeters.

While it is possible for the radius of curvature of the upper portions 550 and the lower portions 552 of the waves to be substantially equal to each other, in certain embodiments, the radius of curvature of the upper portions 550 of the waves 540 is greater than the radius of curvature of the lower portions 552 of the waves 540.

Forming the waves 540 with the radius of curvature of the upper portions 550 being greater than the radius of curvature of the lower portions 552 provides the upper portions 550 with a greater length than the lower portions 552. This configuration increases the ability of the cutting assembly 532 to cut tissue located between the ilium 14 and the sacrum 16.

The radius of curvature of the upper portions 550 of the waves 540 may be between about 0.30 millimeters and about 2 millimeters. In certain embodiments, the radius of curvature of the upper portions 550 of the waves 540 is between about 0.80 millimeters and about 0.90 millimeters.

The radius of curvature of the lower portions 552 of the waves 540 may be between about 0.30 millimeters and about 2 millimeters. In certain embodiments, the radius of curvature of the lower portions 552 of the waves 540 is between about 0.50 millimeters and about 0.60 millimeters.

The waves 540 may be offset from the proximal end of the cutting assembly 532 so that the proximal ends of the two sides of the cutting assembly 532 may be placed adjacent to each other while the lower portions 552 of the waves 540 on the two sides of the cutting assembly 532 are adjacent to each other.

In certain embodiments, the offset from the proximal end and the center of the waves 540 that is intermediate the upper portion 550 and the lower portion 552 is between about 0.40 millimeters and about 2 millimeters. In other embodiments, the offset from the proximal end and the center of the waves 540 that is intermediate the upper portion 550 and the lower portion 552 is between about 0.60 millimeters and about 0.90 millimeters.

Similarly, the waves 540 may be offset from the distal end of the cutting assembly 532 so that the distal end of two cutting assembly 532 may be substantially flat while the lower portions 552 of the waves 540 on the two sides of the cutting assembly 532 are adjacent to each other.

In certain embodiments, the offset from the distal end and the center of the waves 540 that is intermediate the upper portion 550 and the lower portion 552 is between about 0.40 millimeters and about 2 millimeters. In other embodiments, the offset from the distal end and the center of the waves 540 that is intermediate the upper portion 550 and the lower portion 552 is between about 0.60 millimeters and about 0.90 millimeters.

Since the proximal ends of the two sides of the cutting assembly 532 are attached to the other portions of the undercutting system, it may not be necessary to attach the proximal ends of the two sides of the cutting assembly 532 to each other. Similarly, it may not be necessary to fasten the two sides of the cutting assembly 532 to each other proximate the lower portions 552 of the waves 540. Not attaching the proximal ends of the two sides of the cutting assembly 532 and the lower portions 552 of the waves 540 of the two sides of the cutting assembly 532 may increase the flexibility of the cutting assembly 532.

While it is possible to sharpen at least a portion of the side edges of the cutting assembly 532 to increase the ability of the cutting assembly 532 to cut the tissue between the ilium 14 and the sacrum 16, the cutting assembly 532 may be fabricated without sharpening the side edges of the cutting assembly 532.

Even without sharpening, the side edges of the cutting assembly 532 may be sufficiently sharp to cut the tissue between the ilium 14 and the sacrum 16. If the side edges of the cutting assembly 532 are sharpened, the side edges may be too sharp, which could make it more likely that the cutting assembly 532 would cut into the ilium 14 and the sacrum 16.

Even though it is desired to prepare the surfaces of the ilium 14 and the sacrum 16 with the undercutting system, it is generally desirable to not cut too deeply into the ilium 14 and the sacrum 16, as such cutting would not only increase the time associated with preparing the ilium 14 and the sacrum 16 for the sacroiliac fusion but could also negatively impact the strength of the ilium 14 and the sacrum 16.

The undercutting system may include a plurality of cutting assemblies 532 having waves 540 of different heights. One of the cutting assemblies 532 with having the smallest wave height may be initially used. Thereafter, cutting assemblies 532 having progressively larger wave height may be used to form a progressively wider region between the ilium 14 and the sacrum 16.

The cutting assembly 532 having the preceding shape and characteristics may be formed from a variety of materials. A person of skill in the art will appreciate that the material used to fabricate the cutting assembly 532 should be suitable for use within a human body. An example of one such material for fabricating the cutting assembly 532 is nitinol. A beneficial quality of nitinol is that nitinol is bendable but returns to the unbent configuration when the force that caused the bending is removed.

In another embodiment, the undercutting system 610, may include an insertion apparatus 630 and a probe assembly 632 that extends from a distal end of the insertion apparatus 630, as illustrated in FIGS. 21-25.

The insertion apparatus 630 may include an elongated shaft 640 that is formed with a length that enables a proximal end thereof to be positioned outside of the patient's body while a distal end thereof is utilized to the prepare the region between the ilium 14 and the sacrum 16 for the sacroiliac fusion process. In certain embodiments, the length of the elongated shaft 640 is between about 15 centimeters and about 45 centimeters.

The elongated shaft 640 may be formed with a relatively small outer diameter to minimize a size of the aperture 20 that needs to be formed in the ilium 14. The larger the aperture 20 that is formed in the ilium 14, the greater the potential of the ilium 14 weakening to the point at which the ilium 14 is more susceptible to breakage. In certain embodiments, the outer diameter of the elongated shaft 640 is between about 6 millimeters and 20 millimeters.

The insertion apparatus 630 may also include a handle portion 642 proximate a proximal end thereof. The handle portion 642 enhances the ability to manipulate the insertion apparatus 630 such as insertion, rotation and withdrawal.

The handle portion 642 may have a diameter that is greater than a diameter of the elongated shaft 640. In certain embodiments, the handle portion 642 has a diameter of between about 2 centimeters and about 20 centimeters.

An outer edge of the handle portion 642 may have a plurality of concave regions 644 formed therein. The concave regions 644 enhance the ability to grip the handle portion 642 and thereby manipulate the insertion apparatus 630.

The insertion apparatus 630 may further include a control knob 646 that is used for extending and retracting the probe assembly 362. In one configuration of the insertion apparatus 630, the control knob 646 is rotatably mounted with respect to the insertion apparatus 630.

The control knob 646 may have a diameter that is different than a diameter of the handle portion 642. Forming the control knob 646 with a diameter that is different than a diameter of the handle portion 642 minimizes the potential that a person using the insertion apparatus 630 would inadvertently manipulate the insertion apparatus 630 or the control knob 646.

The control knob 646 may have a diameter that is less than a diameter of the handle portion 642. In certain embodiments, the control knob 646 has a diameter of between about 2 centimeters and about 20 centimeters.

An outer edge of the control knob 646 may have a plurality of concave regions (not shown) formed therein. The concave regions enhance the ability to grip the control knob 646 and thereby manipulate the insertion apparatus 630.

Rotation of the control knob 646 in a first direction causes the probe assembly 632 to be extended from the distal end of the insertion apparatus 630. Rotation of the control knob 646 in a second direction, which is opposite the first direction, causes the probe assembly 632 to be retracted into the distal end of the insertion apparatus 630.

The insertion apparatus 630 may also include a lock screw 650 operably attached hereto. The lock screw 650 may be oriented generally transverse to the elongated shaft 40 and may be positioned proximate the handle portion 642. The lock screw 650 may threadably engage the elongated shaft 640.

The lock screw 650 may be positioned in an engaged position where a distal end of the lock screw 650 extends into the interior of the elongated shaft 640 until the distal end engages a shaft that extends between the probe assembly 632 and the control knob 646. The lock screw 650 thereby retains the shaft in a fixed position with respect to the elongated shaft 640 to prevent movement of the probe assembly 632 with respect to the insertion apparatus 630.

Rotating the lock screw 650 in an opposite direction causes the distal end to not engage the cutter shaft so that the shaft may be moved with respect to the elongated shaft 640 to move the probe assembly 632 between the extended and retracted positions.

Figure 24:
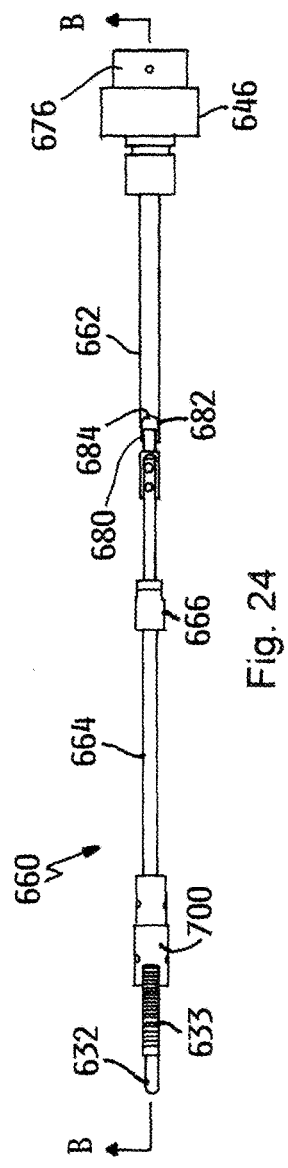
FIG. 24 is an interior portion of the undercutting system of FIG. 21.
Figure 25:
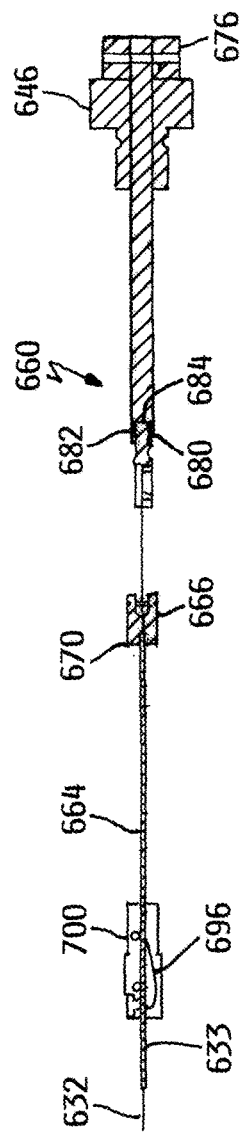
FIG. 25 is a sectional view of the interior portion of the undercutting system of FIG. 6 taken along a line B-B in FIG. 24.

Inside at least a portion of the elongated shaft 640 is a control mechanism 660 that operably attaches the probe assembly 632 to the other portions of the insertion apparatus 630, as most clearly illustrated in FIGS. 22, 24 and 25. A primary function of the control mechanism 660 is to facilitate extension and refraction of the probe assembly 632.

The control mechanism 660 may generally include a first attachment section 662 and a second attachment section 664. The first attachment section 662 is attached to the control knob 646. In one configuration, the first attachment section 662 is fixedly attached to the control knob 646 so that the first section 662 rotates when the control knob 646 is rotated.

The first attachment section 662 may have a length that is less than the length of the elongated shaft 640. In certain embodiments, the first attachment section 662 has a length that is approximately one-half of the length of the elongated shaft 640.

The first attachment section 662 may have a generally cylindrical shape with an outer diameter that is slightly smaller than an inner diameter of the elongated shaft 640, as most clearly illustrated in FIG. 22. Forming the first attachment section 662 with this shape facilitates rotating and sliding of the first attachment section 662 with respect to the elongated shaft 640.

A distal end of the first attachment section 662 has a connection mechanism 666 that facilitates attaching the second attachment section 664 to the first attachment section 662. In one such configuration, the connection mechanism 666 includes a recess 670 formed in the distal end. The recess 670 may have a width and a depth that is greater that a width and a depth of the proximal end of the second attachment section 664.

An attachment pin 672 may be provided in the recess 670 that enables the second attachment section 664 to engage the connection mechanism 666. In certain embodiments, the attachment pin may be oriented generally perpendicular to the first attachment section 662.

An aperture may be formed in the proximal end of the second attachment section 664. The aperture may have a diameter that is slightly larger than a diameter of the attachment pin. Using such a configuration, the attachment pin may extend into the aperture to retain the first attachment section 662 in a fixed relationship with respect to the second attachment section 664.

Forming the connection mechanism 666 with preceding configuration allows the second attachment section 664 to be attached to the first attachment section 662 when the first attachment section 662 and the second attachment section 664 are not covered by the elongated shaft 640.

On the other hand, when the elongated shaft 640 is placed over first attachment section 662 and the second attachment section 664, the second attachment section 664 is retained in engagement with the first attachment section 662.

A person of skill in the art will appreciate that it is possible to attach the first attachment section 662 and the second attachment section 664 using different structures, which enable sliding and rotating of the first attachment section 662 and the second attachment section 664 with respect to the elongated shaft 640.

While the figures illustrate that a mechanical connection is provided between the probe assembly 632 and the other components of the undercutting system 610, it is also possible to utilize an electrical connection between the probe assembly 632 and the other components of the undercutting system 610. Such an electrical connection may utilize switches and actuators. It is also possible to use pneumatic and hydraulic systems to operably connect the probe assembly 632 and the other components of the undercutting system 610.

The connection mechanism 666 may also include a ball-type connector 680 that attaches the connection mechanism 666 to the first attachment section 662. The ball-type connector 680 may include a ball-shaped extension 682 on the connection mechanism 666 and a recess 684 formed in the distal end of the first attachment section 662. The recess 684 has a shape that is generally complementary to the shape of the ball-shaped extension 682.

Similar to the attachment between the connection mechanism 666 and the second attachment section 664, the ball-type connector 680 allows the first attachment section 662 to be attached to the connection mechanism 666 when the first attachment section 662 and the connection mechanism 666 are not covered by the elongated shaft 640.

On the other hand, when the elongated shaft 640 is placed over first attachment section 662 and the connection mechanism 666, the ball-shaped extension 682 is retained in engagement with the recess 684.

The probe assembly 632 is attached to the distal end of the second attachment section 664. To accommodate using probe assemblies 632 having different lengths, the undercutting system 610 may be provided with more than one second attachment section 664 having different lengths. Alternatively or additionally, the undercutting system 610 may include more than one first attachment section 662 having different lengths. Using such a configuration enables one of the first attachment sections 662 and the second attachment sections 664 to be selected based upon the length of the probe assembly 632.

A benefit of using the ball-shaped extension 682 is that this connection mechanism enables the control handle to rotate such as when extending or retracting the probe assembly 632 with respect to the insertion apparatus 630 without having the probe assembly 632 rotate.

The distal end of the second attachment section 664 may have a recess formed therein. The recess may have a depth that is greater than a thickness of the proximal end of the probe assembly 632. The recess may extend across at least a portion of a width of the second attachment section 664.

An attachment pin may be provided in the recess that enables the probe assembly 632 to engage the second attachment section 664. In certain embodiments, the attachment pin may be oriented generally perpendicular to the second attachment section 664.

The second attachment section 664 may be formed with a height and a width that are both slightly smaller than a height and a width of a channel 696 that is formed in an end cap 700, which is discussed in more detail below. Forming the second attachment section 664 with these dimensions enables the second attachment section 664 to slide in the channel 696.

The cap 700 may be positioned in the distal end of the elongated shaft 640, as most clearly illustrated in FIG. 22. The cap 700 thereby seals the elongated shaft 640 to generally restrict tissue and fluid from entering the elongated shaft 640.

While it is possible for a distal end of the cap 700 to be oriented generally transverse to the elongated shaft 640, the distal end of the cap 700 may be oriented at an angle of less than about 90 degrees with respect to the elongated shaft 640. In certain embodiments, the distal end of the cap 700 is oriented at an angle of between about 45 degrees and about 60 degrees.

As referenced above, the cap 700 has the channel 696 formed therein. Proximate the proximal end, the channel 696 may be generally aligned with but offset from a central axis of the elongated shaft 640. Proximate the distal end, the channel 696 may be oriented generally perpendicular to the central axis of the elongated shaft 640.

Intermediate the proximal end and the distal end, the channel 696 is curved. The radius of curvature may be determined by a variety of factors. An example of one such factor is the flexibility of the portion of the probe assembly 632 and the flexibility of the cutting assembly 633.

The channel 696 thereby causes the probe assembly 632 to be deflected such that when the probe assembly 632 extends from the cap 700, the probe assembly 632 is oriented in a direction that is generally transverse to the elongated shaft 640, as illustrated in FIG. 22, so that the probe assembly 632 can be extended into the region between the ilium 14 and the sacrum 16.

Because of the flexibility of the probe assembly 632, it is not necessary that the distal end of the channel 696 be oriented precisely transverse to the central axis of the elongated shaft 640. For example, the distal end of the channel 696 may be oriented slightly towards the ilium 14 to encourage preferential cutting of the ilium 14 because the ilium 14 is harder than the sacrum 16. Alternatively, orienting the distal end of the channel 696 slightly towards the sacrum 16 may allow the angle of curvature within the cap to be reduced.

The cap 700 may have an aperture that extends therethrough that is generally perpendicular to the axis of the elongated shaft 640. The elongated shaft 640 may also include an aperture that is generally aligned with the aperture when the cap 700 is placed into the distal end of the elongated shaft 640. A pin is extended through the aperture and the aperture to thereby retain the cap 700 in a stationary position with respect to the elongated shaft 640.

The cutting assembly 633 may be used in conjunction with the probe assembly 632. To permit the deflection of the cutting assembly 633, the cutting assembly 633 may be fabricated from a flexible material, as is discussed in more detail below. To increase the flexibility of the cutting assembly 633, a plurality of kerfs or notches 642 may be formed in the cutting assembly 633.

As illustrated in FIGS. 26-29, the kerfs 642 may extend through an upper surface 650 of the cutting assembly 633. The kerfs 642 may also extend through at least a portion of at least one of the side surfaces 652 of the cutting assembly 633. The kerfs 642 may also extend into a portion of the lower surface 654 of the cutting assembly 633.

Forming the kerfs 642 with the preceding configuration allows a lower surface 654 of the cutting assembly 633 to be substantially continuous. This configuration provides the cutting assembly 633 with sufficient strength to resist breaking while the cutting assembly 633 is used to cut tissue from between the ilium 14 and the sacrum 16.

The kerfs 642 may be formed with a width that is sufficiently large so that the opposite sides of each of the kerfs 642 do not contact each other while the cutting assembly 633 is deflected from the initial orientation that is generally aligned with but offset from the center axis of the insertion apparatus 630 to a deflected orientation that is generally transverse to the central axis of the insertion apparatus, as the cutting assembly 633 exits the distal end of the cap 700.

In certain embodiments, the kerfs 642 may have a width of up to about 1 millimeter. In other embodiments, the kerfs 642 may have a width that is between about 0.4 millimeters and about 0.6 millimeters.

The kerfs 642 also decrease the smoothness of the cutting assembly 633. Contact between the kerfs 642 and the tissue between the ilium 14 and the sacrum 16 could cause such tissue to be abraded or cut and thereby facilitate preparation of the region between the ilium 14 and the sacrum 16 for the sacroiliac fusion process.

While the figures illustrate that the kerfs 642 are formed on one side of the cutting assembly 633, it is possible for the kerfs 642 to be formed on both sides of the cutting assembly 633. If the kerfs 642 are formed on both sides of the cutting assembly 633, the kerfs 642 on the opposite sides may be offset so that the kerfs 642 do not unduly weaken the cutting assembly 633.

Whether the kerfs 642 are formed in one side or both sides of the cutting assembly 633, the kerfs 642 should not occupy too great a portion of the cutting assembly 633 such that the cutting assembly 633 is likely to bend or kink during the process of deflecting during the extension or retraction of the cutting assembly 633 from the insertion apparatus 630 as well as during the use of the cutting assembly 633 to cut tissue from between the ilium 14 and the sacrum 16.

Depending on the material from which the cutting assembly 633 is formed, it may be possible to use other techniques that provide the cutting assembly 633 with a desired degree of flexibility.

In addition to or as an alternative to kerfs for roughening the outer surface of the cutting assembly 633, it is possible to use other techniques to enhance the ability of the cutting assembly 633 to cut through tissue between the ilium and the sacrum as well as to cut into the ilium and the sacrum. An example of one such technique that may be used to roughen the outer surface of the cutting assembly 633 is to provide an abrasive on at least a portion of the outer surface of the cutting assembly 633.

However, it should be noted that the fact that the cutting assembly 633 may be supported by the probe assembly 632, which extends through the bore 640 in the cutting assembly 633.

The cutting assembly 633 having the preceding shape and characteristics may be formed from a variety of materials. A person of skill in the art will appreciate that the material used to fabricate the cutting assembly 633 should be suitable for use within a human body. An example of one such material for fabricating the cutting assembly 633 is nitinol. A beneficial quality of nitinol is that nitinol is bendable but returns to the unbent configuration when the force that caused the bending is removed.

At least one cutting element 634 may be provided on the cutting assembly 634. The cutting element 634 may be positioned proximate the distal end of the cutting assembly 633. In certain embodiments, the cutting element 634 may include a main cutter portion 660 and at least one extension portion 662 that extends from the main cutter portion 660.

The main cutter portion 660 may have a height that is greater than the height of the cutting assembly 634. The main cutter portion 660 thereby enables a region between the ilium 14 and the sacrum 16 having a greater thickness to be prepared.

The main cutter portion 660 may have a height that is no greater than an inner diameter of the elongated shaft 640. Forming the main cutter portion 660 with such a configuration enables the cutting assembly 633 to be positioned substantially within a profile of the elongated shaft 640 when the cutting assembly 633 is in a retracted configuration so that the cutting assembly 633 does not interfere with the insertion of the distal end of the undercutting system 610 extending through the aperture 20 in the ilium 14.

The main cutter portion 660 may have a height of between about 1 millimeter and about 3 millimeters. In certain embodiments, the main cutter portion 660 may have a width of about 2 millimeters.

Similarly, the main cutter portion 660 may have a width that is no greater than an inner diameter of the elongated shaft 640. Forming the main cutter portion 660 with such a configuration enables the cutting assembly 633 to be positioned substantially within a profile of the elongated shaft 640 when the cutting assembly 633 is in a retracted configuration so that the cutting assembly 633 does not interfere with the insertion of the distal end of the undercutting system 610 extending through the aperture 20 in the ilium 14.

The main cutter portion 660 may have a width of between about 2 millimeters and about 5 millimeters. In certain embodiments, the main cutter portion 660 may have a width of about 3 millimeters.

The main cutter portion 660 may extend along at least a portion of the upper surface 650 and the lower surface 654. In certain embodiments, the main cutter portion 660 extends substantially around the entire cutting assembly 633.

The main cutter portion 660 may be curved proximate each of the corners thereof. Using the curved corners reduces the potential of the main cutter portion 660 digging into the surface of the ilium 14 or the sacrum 16 while the cutting assembly 633 is rotated.

In other embodiments, where it is desired to enhance the cutting ability of the cutting assembly 633, the main cutter portion 660 may be formed with sharp corners and at least a portion of the surface of the corners may be sharpened to enhance the cutting ability of the main cutter portion 660.

The main cutter portion 660 has a distal edge and a proximal edge that are disposed at opposite ends thereof. In certain embodiments, the distal edge and the proximal edge may be sufficiently sharp to cut through the tissue between the ilium 14 and the sacrum 16 that comes into contact with at least one of the distal edge and the proximal edge.

Alternatively, at least one of the distal edge and the proximal edge may include a cutting surface. In certain embodiments, cutting surfaces are provided on both distal and proximal edges of the main cutter portion 660. Providing the cutting surfaces on the distal and proximal edges enhances the ability of the main cutter portion 660 to cut through tissue between the ilium 14 and the sacrum 16 as the cutting assembly 633 is rotated.

The extension portion 662 may have a generally planar configuration that extends from at least one of the upper and lower surfaces of the main cutter portion 660. While not illustrated, it is also possible for at least one of the extension portions 662 to be positioned on the side surfaces of the main cutter portion 660.

In certain embodiments, the extension portion 662 may extend in substantially equal distances on opposite sides of the main cutter portion 660. The extension portion 662 may have a generally rectangular shape that is defined by a distal edge 670 and a pair of side edges 672.

While it is illustrated that a height of the extension portion 662 is approximately equal on opposite sides of the main cutter portion 660, it is possible to configure the extension portion 662 so that the height of the extension portion 662 is not approximately equal on opposite sides of the main cutter portion 660.

The height of the distal edge 670 may be limited by the inner diameter of the elongated shaft 40 so that the cutting element 634 may be retracted within the insertion apparatus 630 when the insertion apparatus 630 is inserted into and removed from the region between the ilium 14 and the sacrum 16.

In certain embodiments, the height of the extension portion 662 on opposite sides of the main cutter portion 660 is between about 1 millimeter and about 5 millimeters. In other embodiments, the height of the extension portion 662 on opposite sides of the main cutter portion 660 is about 3 millimeters.

In certain embodiments, a width of the extension portion 662 is approximately the same on opposite sides of the main cutter portion 660. The width of the extension portion 662 may be between about 1 millimeter and about 5 millimeters. In other embodiments, the width of the extension portion 662 is about 3 millimeters.

Corners proximate the intersection of the distal edge 670 and each of the side edges 672 may be curved. While such curvature could reduce the cutting ability of the extension portion 662 that could be attained if the distal edge 670 and the side edge 672 intersected at a corner, this curvature may reduce the tendency of the extension portion 662 to dig too deeply into the surfaces of the ilium 14 and the sacrum 16. As a result of this configuration, the extension portion 662 would preferentially cut into the tissue between the ilium 14 and the sacrum 16 as opposed to cutting the ilium 14 and the sacrum 16.

While it is illustrated that the extension portion 662 has a substantially equal thickness, it is possible for the thickness of the extension portion 662 to vary. In certain embodiments, the thickness of the extension portion 662 may be greater proximate to the main cutter portion 660 to resist bending or deformation of the cutting element 634.

In certain embodiments, a thickness of the extension portion 662 may be between about 0.2 millimeters and about 2 millimeters. In other embodiments, the thickness of the extension portion 662 may be about 0.5 millimeters.

While it is illustrated that the thickness of the extension portion 662 is approximately equal on opposite sides of the main cutter portion 660, it is possible to configure the extension portion 662 so that the thickness of the extension portion 662 is not approximately equal on opposite sides of the main cutter portion 660.

The edge of the extension portion 662 proximate the distal ends thereof may be sufficient to cut through the tissue between the ilium 14 and the sacrum 16. Using the extension portion 662 without the sharpened edges may reduce a tendency of the extension portion 662 to cut into the ilium 14 and the sacrum 16 while the cutting assembly 633 is rotated.

Alternatively, the edge of the extension portion 662 proximate the distal ends thereof may be sharpened to facilitate cutting of tissue proximate the surfaces of the ilium 14 and the sacrum 16 while the cutting assembly 633 is rotated.

Figure 26:
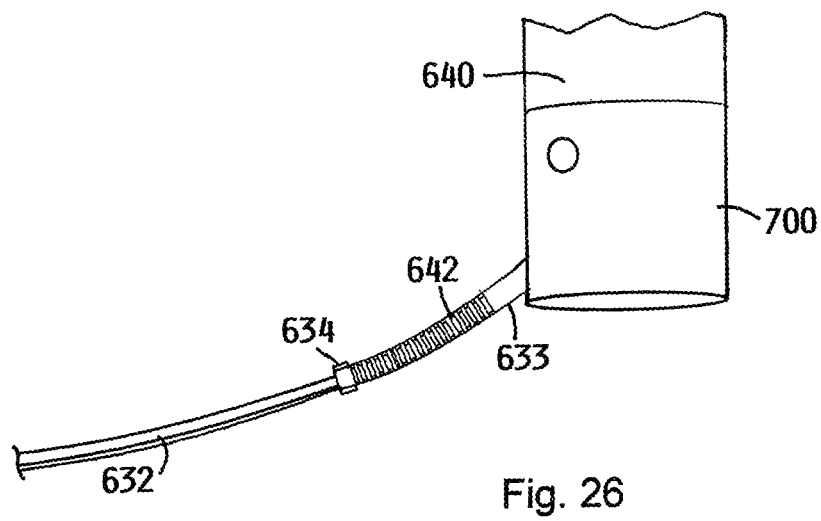
FIG. 26 is a side view of a cutting assembly extending over the probe assembly.
Figure 27:
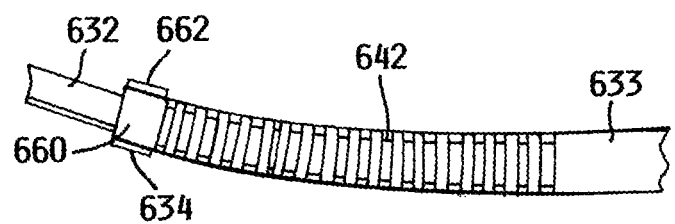
FIG. 27 is a perspective view of the cutting assembly extending over the probe assembly.
Figure 28:
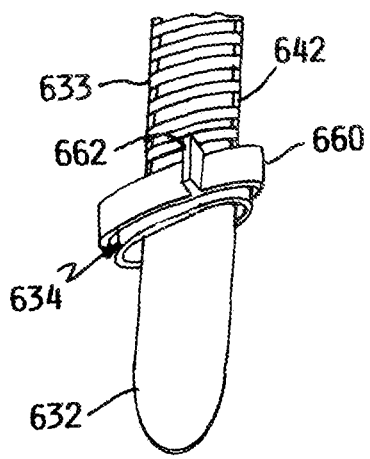
FIG. 28 is an end view of the cutting assembly extending over the probe assembly.
Figure 29:
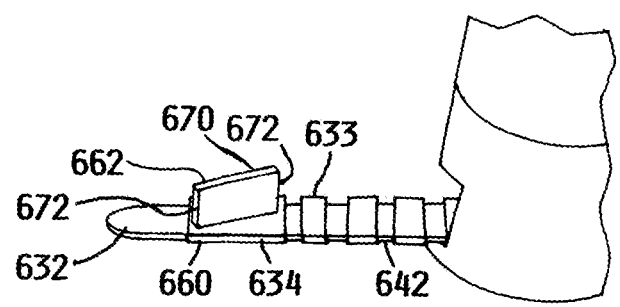
FIG. 29 is a perspective view of another configuration of the cutting assembly extending over the probe assembly.

The extension portion 662 may be oriented generally parallel to the length of the cutting element 634, as illustrated in FIGS. 26-28. In other embodiments, the extension portion 662 may be oriented at an angle of between about 0 degrees and about 60 degrees with respect to a length of the cutting element 634, as illustrated in FIG. 29. In other embodiments, the angle between the extension portion 662 and the main cutter portion 660 may be about 30 degrees.

Orienting the extension portion 662 at the angle with respect to the length of the main cutter portion 660 causes one of the edges to be disposed forwardly. Such a configuration may increase the ability of the cutting element 634 to cut tissue from between the ilium 14 and the sacrum 16 as the cutting assembly 634 is rotated.

While it is illustrated that the extension portion 662 is oriented generally transverse to the surface of the main cutter portion 660, it is possible for the extension portion 662 to be oriented at an angle with respect to the surface of the main cutter portion 660.

While it is possible for the cutting element 634 to be placed at the distal end of the cutting assembly 633, in certain embodiments, the cutting element 634 is mounted a distance from the distal end of the cutting assembly 633. Mounting the cutting element 634 a distance from the distal end of the cutting assembly 633 enables the cutting assembly 633 to define a path through the tissue between the ilium 14 and the sacrum 16, as opposed to the cutting element 634 being the primary component that defines the path through the tissue between the ilium 14 and the sacrum 16.

The extension portion 662 may be positioned at a location that is approximately intermediate between the side edges of the main cutter portion 660. Placing the extension portion 662 in this location may reduce twisting of the cutting assembly 633, which could potentially occur if the extension portion 662 was located closer to one of the side edges of the main cutter portion 660.

The cutting element 634 having the preceding shape and characteristics may be formed from a variety of materials. A person of skill in the art will appreciate that the material used to fabricate the cutting element 634 should be suitable for use within a human body. An example of one such material for fabricating the cutting element 634 is nitinol.

In certain embodiments, the cutting assembly 633 may be fabricated separately from the cutting element 634. Forming the structure in this manner enables different materials to be used for fabricating the cutting assembly 633 and the cutting element 634 so that the respective materials may be optimized based upon the function of the associated structure.

The cutting element 634 may be attached to the cutting assembly 633 using a variety of techniques that cause the cutting element 634 to be fixedly attached to the cutting assembly 633. One such suitable technique for attaching the cutting element 634 to the cutting assembly 633 is welding.

Alternatively, it is possible to fabricate the cutting assembly 633 and the cutting element 634 as a single unit such as by machining a block to provide a substantially flat cutting assembly 633 and a cutting element 634 that extends from the cutting assembly 633.

The undercutting system 610 may include a plurality of cutting assemblies 632 with cutting elements 634 having different distances thickness. One of the cutting assemblies 632 with the cutting element 634 having the smallest thickness may be initially used. Thereafter, cutting assemblies 632 with cutting elements 634 having progressively larger thicknesses may be used to form a progressively wider region between the ilium and the sacrum.

In addition to or in an alternative to forming the cutting elements 634 with different thicknesses, it is possible to use a series of cutting elements 634 to facilitate preparing the surfaces of the ilium 14 and the sacrum 16 in a predictable manner. In one such configuration, there is a series of three cutting elements 634 used to prepare the region between the ilium 14 and the sacrum 16.

The first cutting element 634 may be configured to preferentially cut tissue on the ilial side of the first cutting element 634. The first cutting element 634 may have one extension portion 662 that is positioned on the ilial side of the first cutting element 634.

The extension portion 662 may have a first height that extends above a surface thereof. In certain embodiments, the extension portion 662 may have a height of about 0.5 millimeters. The overall height of the first cutting element 634 is thereby about 2.5 millimeters.

Because the extension portion 662 is on the ilial side of the first cutting element 634, this configuration may exhibit beneficial performance characteristics because this configuration accounts for the fact that a surface of the ilium 14 is harder than a surface of the sacrum 16.

The second cutting element 634 may also include one extension portion 662 that is positioned on the ilial side of the first cutting element 634. The extension portion 662 on the second cutting element 634 may have a height that is greater than the height of the extension portion 662 on the first cutting element.

The extension portion 662 may have a second height that extends above a surface thereof. In certain embodiments, the extension portion 662 may have a height of about 1 millimeter. The overall height of the first cutting element 634 is thereby about 3 millimeters.

The configuration of the second cutting element 634 thereby enables an increased distance area between the ilium 14 and the sacrum 16 to be prepared, as compared to the first cutting element 634. However, similar to the first cutting element 634, the second cutting element 634 preferentially cuts on the ilial side of the second cutting element 634.

The third cutting element 634 may have an extension portion 662 that is positioned on the ilial and sacral sides thereof. While it is possible for the extension portions 662 to have different heights, in certain embodiments, the extension portions 662 each have a height of about 1 millimeter. The overall height of the third cutting element 634 is thereby about 4 millimeters.

Because the extension portions 662 are positioned on the ilial and sacral sides of the third cutting element 634, the third cutting element cuts tissue that is located on the ilial and sacral side of the third cutting element 634.

The cutting assembly 633 may be operably attached to the insertion apparatus 630 to facilitate extension and refraction of the cutting assembly 633 with respect to the insertion apparatus 630. In one embodiment, a control is provided for movement of the cutting assembly 132 that is separate from the control knob 646 used to move the probe assembly 632.

The cutting assembly control may be a knob 676 that is mounted to the insertion apparatus. Similar to the control knob 646, rotation of the cutting assembly control knob 676 in a first direction may cause extension of the cutting assembly 633 from the insertion apparatus 630 and rotation of the cutting assembly control knob 676 in a second direction may cause retraction of the cutting assembly 633 into the insertion apparatus 630.

In another embodiment, the probe assembly 632 and the cutting assembly 633 are both operably connected to the control knob 646. When the control knob 646 is initially rotated, the probe assembly 632 is extended progressively further from the insertion apparatus 630. Once the probe assembly 632 reaches its maximum extension, continued rotation of the control knob 646 causes the cutting assembly 633 to be extended from the insertion apparatus 630.

When the surgical procedure is completed and it is desired to remove the undercutting system, the control knob 646 is rotated in an opposite direction. This rotation initially causes retraction of the cutting assembly 633.

As illustrated in FIGS. 26-28, the distal end of the probe assembly 632 extends beyond the distal end of the cutting assembly 633 when these components are extended from the distal end of the insertion apparatus 630. Using this configuration enables the probe assembly 632 to guide the cutting assembly 633 and thereby reduce the potential of the cutting assembly 633 digging too deeply into the ilium 14 or the sacrum 16.

Once the probe assembly 632 has been extended the maximum distance from the distal end of the insertion apparatus 630 and the insertion apparatus 630 has been rotated at least one full revolution so that the probe assembly 632 has caused the path between the ilium 14 and the sacrum 16 to be defined, it may be possible for the cutting assembly 633 to be fully extended so that the distal end of the cutting assembly 633 is at approximately the same distance from the distal end of the insertion apparatus 630 as the probe assembly 632.

Once the cutting assembly 633 is fully retracted, continued rotation of the control knob 46 causes the probe assembly 632 to be retracted. After both the probe assembly 632 and the cutting assembly 633 are fully refracted within the insertion apparatus 630, the undercutting system may be removed from the patient.

Using the probe assembly 632 in conjunction with the cutting assembly 633 enables the region between the ilium 14 and the sacrum 16 to be prepared for the sacroiliac fusion while minimizing the cutting assembly 633 digging into the surface of the ilium 14 or the sacrum 16.

While it is desirable to prepare the surfaces of the ilium 14 and the sacrum 16 by exposing bleeding bone, it is desirable to avoid the cutting assembly 633 digging into the surface of the ilium 14 or the sacrum 16 too deeply. When the cutting assembly 633 digs too deeply into the surface of the ilium 14 or the sacrum 16, it becomes more difficult to rotate the cutting assembly 633 because the ilium 14 and the sacrum 16 are much harder than the tissue located between the ilium 14 and the sacrum 16. The cutting assembly 633 having the characteristics set forth above meets these criteria.

To minimize the potential of the cutting assembly breaking during the cutting process, a clutch mechanism may be provided between the handle and the cutting assembly. The clutch mechanism causes the operable connection between the handle and the cutting assembly to release when greater than a threshold force is encountered. When this occurs, the handle rotates with respect to the cutting assembly.

An audible notification may be provided to indicate to the person operating the cutting assembly that the clutch has been engaged. An example of which such audible notification is a scratching sound that is sufficiently loud to be heard outside of the patient.

After the clutch has been activated, the person operating the cutting assembly may rotate the cutting assembly in an opposite direction or partially retract the cutting assembly. Thereafter, the cutting process may be resumed.

In operation, to facilitate use of the undercutting system 10 and the performance of the sacroiliac fusion, the patient on which the sacroiliac fusion is to be performed may be positioned in a prone orientation on an operating room table or other support structure that is used in conjunction with this procedure.

While it is possible to form a relatively large incision and then pull back the tissue between the skin and the ilium so that the surface of the ilium could directly be viewed when using the undercutting system 10 of the invention, such a process could cause more damage to the tissue between the skin and the ilium, which could increase the time for the patient to recover from the surgical procedure.

The tissue penetrated when using the method discussed herein may include (when moving from lateral to medial)—skin, gluteus maximus, gluteus medius, gluteus minimus, lateral ilium cortex, medial ilium cortex, sacroiliac joint cartilage (ilium and sacrum), lateral sacral cortex, sacral ala, sacral vestibule (which is also known as alar root, sacral pedicle and sacral isthmus) and sacral vertebral body.

Other critical soft tissue that is proximate to where the undercutting system 10 is being used may include (when moving from lateral to medial)—superior cluneal nerves, superior gluteal artery and vein, L4, L5, S1 and S2 nerve roots, iliac artery, iliac vein, sacral foris also known as neuroforamina), bowels and sacral canal.

Additional relevant anatomical landmarks that have not been previously mentioned include greater sciatic notch, alar slope and iliac cortical density, sacral prominence, pubic symphysis, pelvic brim/arcuate line and S1 end plate.

Figure 30:
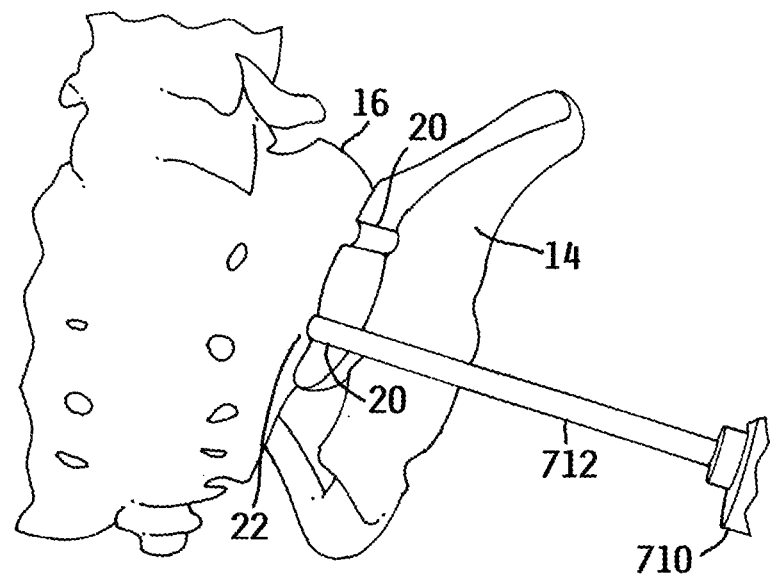
FIG. 30 is a partially cut away perspective view of an aperture being drilled in the sacrum and the ilium as an initial step in a sacroiliac fusion procedure.

After appropriate preparation of the patient and identification of the location for the sacroiliac fusion, at least one aperture 20 is drilled through the ilium 14. This aperture 20 may also at least partially extend into the sacrum 16, as illustrated in FIG. 30. In certain embodiments, there are three apertures drilled.

In certain embodiments, the aperture 20 is oriented generally transverse to the ilium 14, as illustrated in FIG. 30. In other embodiments, an angle between the aperture 20 and the ilium 14 may be between about 45° and about 135°. Fluoroscopic imaging may be used to determine the orientation of the aperture 20.

Orienting the aperture 20 at an angle in the preceding range limits the bending of the probe assembly 632 and the cutting assembly 633 if angles greater to or less than the preceding range were used. Using such angles would require the probe assembly 632 and the cutting assembly 633 to be formed from a more flexible material.

Even though FIGS. 30-33 illustrate that the procedure is performed by initially drilling into the ilium 14, it is also possible to perform the sacroiliac fusion by initially drilling into the sacrum 16. In certain circumstances, it may present fewer challenges in gaining access for the sacroiliac fusion by initially drilling into the ilium 14.

A conventional surgical drill 710 and drill bit 712 may be utilized to form the aperture 20. The aperture 20 may be formed with a diameter that is selected based upon a diameter of the bone screw 620 that will be inserted into the aperture 20 as part of the sacroiliac fusion process.

As illustrated in FIG. 30, the drill may be oriented generally transverse to a surface of at least one of the ilium 14 and the sacrum 16 proximate to where the aperture 20 is being formed. A person of skill in the art will appreciate that neither the sacrum 16 nor the ilium 14 are substantially flat. Additionally, the adjacent surfaces of the ilium 14 and the sacrum 16 may not be substantially parallel to each other proximate to where it is desired to form the aperture 20.

The apertures 20 may include a first aperture 20a that is used in conjunction with a first screw having a diameter of about 12.5 millimeters. In this situation, the drill bit used to form the first aperture 20a may have a diameter of approximately 9 millimeters.

The first aperture 20a may be formed across the sacroiliac joint at the S1 level. The first aperture 20a may be positioned to favor an anterior-inferior side of the sacroiliac joint. The first aperture 20a may be oriented at an angle so that the distal end of the first screw is slightly posterior and superior of a proximal end of the first screw.

The apertures 20 may also include a second aperture 20b that is used in conjunction with a second screw having a diameter of about 6.5 millimeters. In this situation, the drill bit used to form the second aperture 20b may have a diameter of approximately 5 millimeters.

The second aperture 20b may be formed across the sacroiliac joint proximate to where the first aperture 20a is formed in the sacroiliac joint. The second aperture 20b may be oriented at an angle so that the distal end of the second screw is slightly anterior and superior to a proximal end of the second screw.

A variety of techniques may be used to determine the location at which the first aperture 20a and the second aperture 20b are to be formed in the ilium as well as the orientation of the ilium so that the first aperture 20a and the second aperture 20b may be in a desired position and not result in damage to the tissue adjacent to and/or above where the first aperture 20a and the second aperture 20b are to be formed.

A non-limiting example of a technique that may be used to determine the location and orientation of the first aperture 20a and second aperture 20b is a fluoroscope. To assist in evaluating the location and orientation of the anatomical structures proximate to where the undercutting system 10 will be used, it is possible to perform the fluoroscopic imaging from multiple directions.

One such direction for the fluoroscopic imaging is a lateral view across the patient's pelvis. The lateral sacral view provides a visualization of the starting point for the sacroiliac joint access by best showing critical boundaries of the safe bony corridor such as the anterior sacral cortex and the alar slope.

While less clear but also visible, the lateral sacral view provides the ability to see the sacral neural foramina and the spinal canal. The lateral view along with the outlet view can help to identify sacral dysmorphism, a challenging anatomical variation that could lead to a possible contraindication relating to the use of the undercutting system.

The lateral view may be obtained by aligning the projections of the two greater sciatic notches and the two iliac cortical densities. To minimize the x-ray exposure, it is not necessary for there to be exact alignment of the preceding elements.

If the greater sciatic notches and the iliac cortical densities are not simultaneously aligned, it is possible to split the difference between these components. Alternatively, when alignment of the iliac cortical densities is difficult, alignment of the greater sciatic notches may be sufficient for performing the lateral fluoroscopic image.

It should also be noted that when aligning for the lateral view, true lateral of the sacrum may not appear to be true lateral to the patient. For the purposes of this invention, the important facture is the alignment of the sacrum.

Another view for the fluoroscopic imaging is an anteroposterior view with a caudal tilt. This view, which is referred to as the inlet view, may provide an excellent mediolateral view of the advancing guide pin and/or bone screw. This view also best enables avoidance of the posterior spinal canal and the anterior limit of the sacrum.

The inlet view is used in conjunction with the outlet view, which is described below, while advancing the guide pin or bone screw medially into the patient. Together the inlet view and the outlet view provide orthogonal images to guide screw insertion in all three dimensions.

The inlet view is obtained by tilting the fluoroscopic receiver caudal from the anteroposterior position. The device is aligned with a line created by the anterior-inferior sacral cortex and the iliac pelvic brim with the second foramina. To minimize the x-ray exposure, it is not needed for there to be perfect alignment of the inlet view.

Still another view of the fluoroscope imaging is an anteroposterior view with a cephalad tilt. This view, which is referred to as the outlet view, may provide an excellent mediolateral view of the advancing guide pin and bone screw towards the center of the sacral body. The outlet view enables avoidance of the Superior S1 end-plate and the S1 neuroforamina.

The outlet view may be used in conjunction with the inlet view while advancing the guide pin or bone screw medially into the patient. When viewed together, the inlet view and the outlet view provide orthogonal image to guide screw insertion in all three dimensions.

The outlet view is best suited for viewing the sacroiliac joint to facilitate cartilage excision. While the outlet view may be similar to a "Judet" view, it is distinct from such a view and, as such, these views are not interchangeable.

The outlet view assure that the tip of the guide pin is cephalad to the sacral nerve foramen. The outlet view also distinguishes the cephalad border of the sacrum, which is actually the posterior sacral alar region. The anterior aspects of the sacral alar are sloped inferiorly relative to the posterior sacral alar region. The failure to account for this forward sloping could result in the extraosseus screw placement being dangerously close to the iliac vessels and/or the fifth lumbar nerve root.

The outlet view may be obtained by tilting the fluoroscope receiver cephalad from an anteroposterior position until the top of the symphysis pubis is located at the S2 body. To minimize x-ray exposure, it is not needed for there to be perfect alignment of the outlet view.

As an initial point in locating a location for access, a relatively small guide pin such as having a length of about 3 millimeters is held to the outside of the patient proximate to the location of the iliosacral corridor. The tip of the guide pin may be positioned caudal to the iliac cortical density and cephalad to the interosseous path of the upper sacral nerve root.

The lateral projection of the iliosacral corridor identifies the safest position for the distal end of the bone screw that is inserted laterally. The proximal entry point may be outside the iliosacral corridor.

The guide pin tip can be located within the midportion of the alar bone on the lateral image. The iliosacral corridor is the best location for passage of the bone screw using in conjunction with the sacroiliac fusion.

After marking the skin, a vertical incision having a length of between about 2 and 4 centimeter is formed in the skin. Next, using blunt dilation, a probe is extended through the tissue in line with the future path of the screw until reaching the ilium bone.

The most effective area for joint preparation may be the inferior-anterior edge of the safe zone closer to the articular cartilage portion of the joint as opposed to the interosseous portion directly lateral of the safe zone.

The articular portion of the joint is more flat, which is advantageous to encourage fusion at the articular portion of the sacroiliac joint. In contrast, the interosseous portion of the joint, which is posterior to the safe zone, is steeply angulated from perpendicular, and very lumpy and irregular.

Next, the undercutting system 10 is positioned in a retracted configuration so that the probe assembly 32 does not interfere with the insertion process. The distal end of the undercutting system 10 is extended into the aperture 20, as illustrated in FIG. 31.

Figure 32:
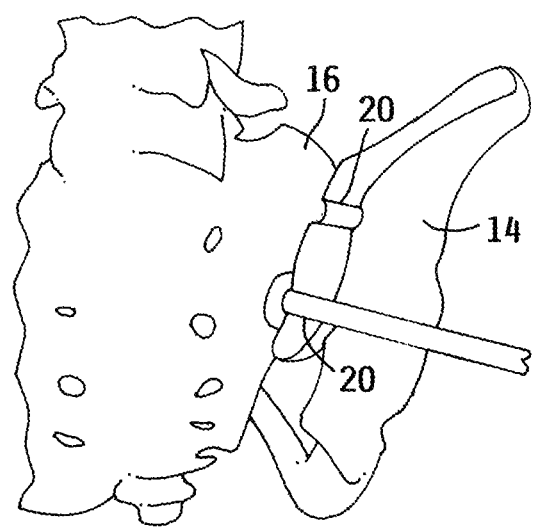
FIG. 32 is a partially cut away perspective view of the undercutting system being used to form an undercut region between the sacrum and the ilium.

Once the distal end of the undercutting system 10 is positioned between the ilium 14 and the sacrum 16, the probe assembly 32 is moved to an at least partially extended configuration, as illustrated in FIG. 32.

The undercutting system 10 is rotated to so that the probe assembly 32 causes a path to be defined between the ilium 14 and the sacrum 16. By defining the path using the probe assembly 32, the potential of the cutting assembly 132 digging too deeply into the ilium 14 or the sacrum 16 is reduced.

Next, the cutting assembly 132 is slid over the probe assembly 32 until the cutting element 134 extends from the distal end of the insertion apparatus 30 and is positioned between the ilium 14 and the sacrum 16. The undercutting system 10 is rotated so that the cutting element 134 contacts tissue between the ilium 14 and the sacrum 16 to cause such tissue to be cut into pieces. Alternatively or additionally, the cutting element 134 may cause cartilage and/or tissue to be scraped from the surface of at least one of the ilium 14 and the sacrum 16. If it is desired to prepare a region having a larger diameter, the cutting assembly 132 may be advanced further and then the undercutting system 10 may be rotated.

Depending on a variety of factors such as the sharpness of the cutting assembly 32 and the hardness of the material being cut, it may not be possible to merely cut through the cartilage and bone using just a rotational motion. Rather, it may be necessary to alternate rotating the undercutting system in clockwise and counter clockwise directions to increase the area that is prepared. The control knob can be periodically rotated to cause the cutting assembly 32 to extend progressively further from the undercutting system 10. While in many circumstances, it may be desirable to prepare a circular area, it is also possible to use the concepts of the invention to prepare a semi-circular area.

Alternatively or additionally, the probe assembly 32 may be withdrawn and a cutting assembly such as is illustrated in FIGS. 21-25 may be used to cut tissue in the region between the ilium 14 and the sacrum 16 that has been defined by the probe assembly 32.

Contact between the cutting assembly 132 and the inner surfaces of the ilium 14 and the sacrum 16 causes the respective surfaces to be abraded to create bleeding bone, which may be desirable to facilitate bone growth between the ilium 14 and the sacrum 16 as part of the sacroiliac fusion process.

A variety of techniques may be used to evaluate the amount of cartilage that has been removed and the extent to which the surfaces of the ilium and the sacrum have been prepared. Examples of such suitable techniques include monitoring the sound emitted during the cutting process, as the cutting of bone may make a scraping sound.

The person operating the undercutting system may monitor the performance of the process using the feel of the cutting head, as it may be more difficult for the cutting head to cut through the ilium and the sacrum than the cartilage.

It is also possible to monitor the progress of the preparation for the sacroiliac fusion using a fluoroscope. While these techniques are described individually, it is possible for one or more of the preceding techniques to be combined.

In certain embodiments, the bits of cartilage and other tissue from between the ilium 14 and the sacrum 16 may become caught in the cutting assembly during the cutting process. In such a situation, the cartilage and other tissue are removed from between the ilium 14 and the sacrum 16 when the cutting assembly is retracted.

It may be necessary to clean the cutting assembly and then reinsert the cutting assembly into the region between the ilium 14 and the sacrum 16 to remove additional bits of the cartilage and other tissue.

Alternatively or additionally, a technique may be utilized to remove the bits of cartilage and other tissue from between the ilium 14 and the sacrum 16. One suitable apparatus that may be used for remove the bits of cartilage and other tissue is a radial deployment surgical tool, which is described in U.S. application Ser. No. 12/941,763, which was filed with the U.S. Patent & Trademark Office on Nov. 8, 2010, and which is assigned to the assignee of the present patent application.

Another technique for removing the cut up bits of cartilage is to flush the region with a fluid and then suction out the water with the cut up bits of cartilage. The process may be repeated until a desired amount of the cut up bits of cartilage is removed from between the ilium and the sacrum.

After the surfaces of the ilium and the sacrum have been prepared, a bone graft may be inserted. Then, a variety of techniques may be used to maintain the ilium and the sacrum in a fixed position with respect to each other. Examples of suitable fixation techniques include bone screws, cannulated screws, pins, cages, glue, coupled device with ball and socket and Herbert screws.

Figure 33:
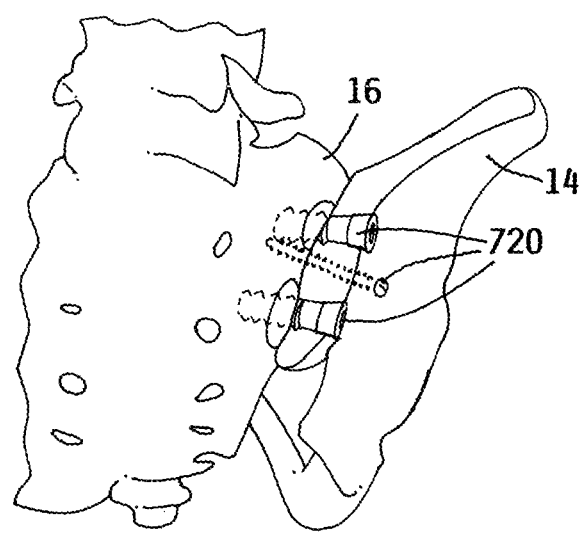
FIG. 33 is a partially cut away perspective view of fasteners inserted into the apertures.
Figure 34:
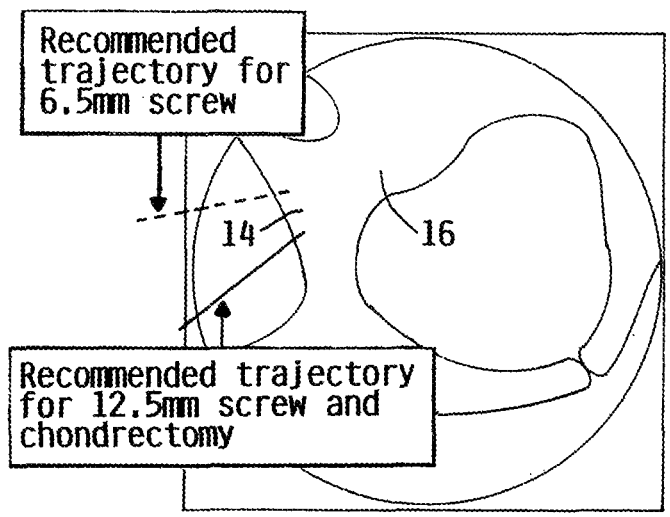
FIG. 34 is an inlet fluoroscope view illustrating a desired trajectory for the two fasteners.
Figure 35:
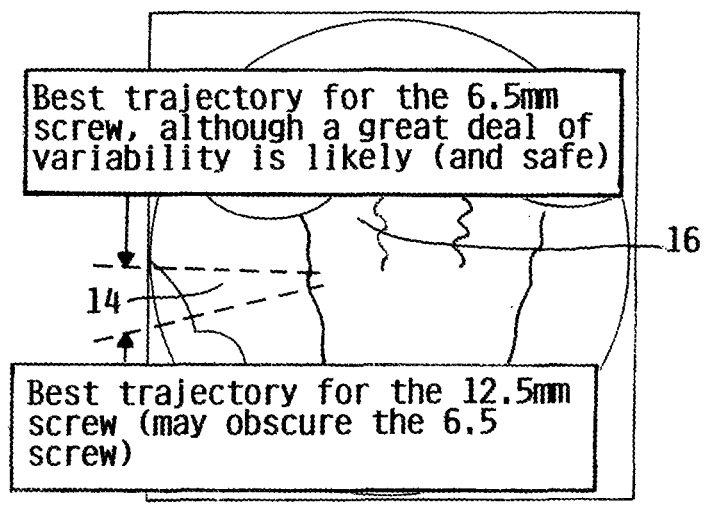
FIG. 35 is an outlet fluoroscope view illustrating a desired trajectory for the two fasteners.
Figure 36:
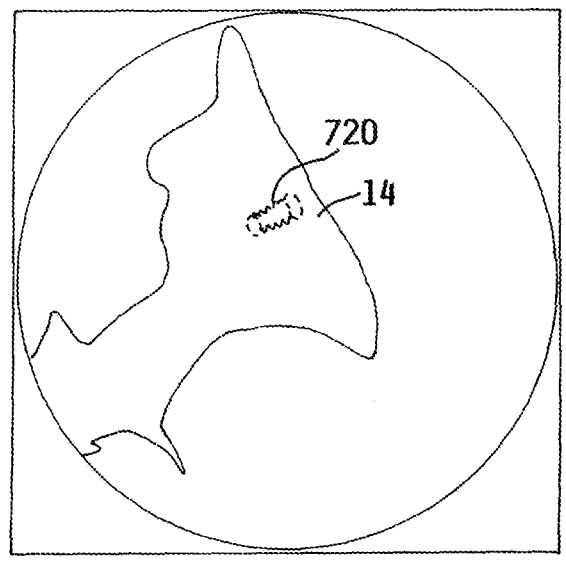
FIG. 36 is a lateral fluoroscope view of the pelvic region after two fasteners have been inserted.
Figure 37:
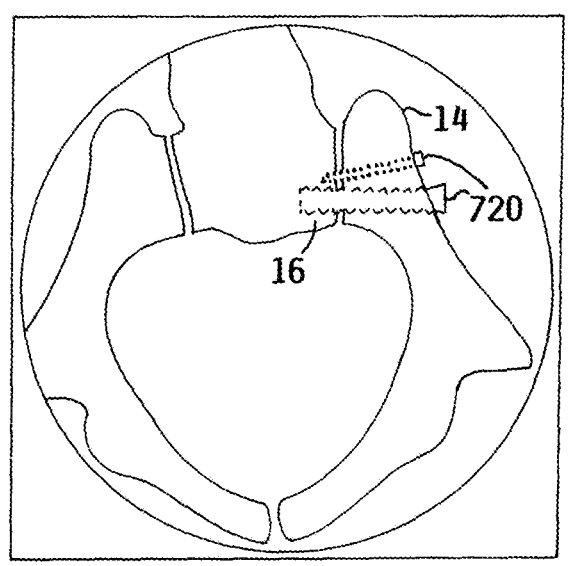
FIG. 37 is an inlet fluoroscope view of the pelvic region after two fasteners have been inserted.
Figure 38:
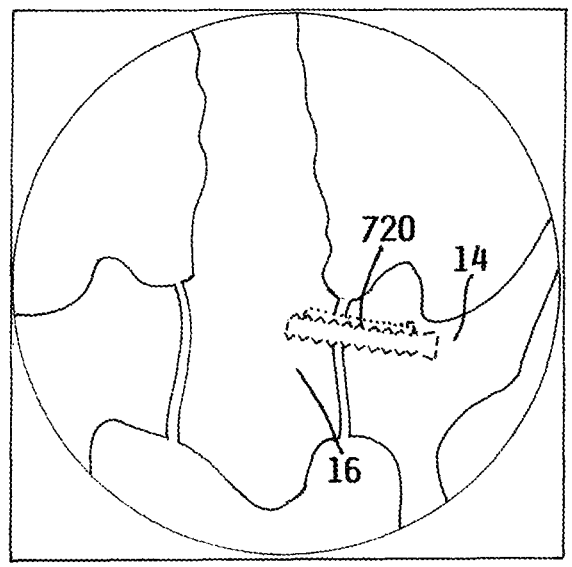
FIG. 38 is an outlet fluoroscope view of the pelvic region after two fasteners have been inserted.

Thereafter, bone screws 720 may be inserted into each of the apertures 20, as illustrated in FIG. 33. The bone screws 620 will be effective at maintaining the ilium 14 and the sacrum 16 in a stationary position with respect to each other as bone grows between the ilium 14 and the sacrum 16 to cause fusion of the ilium 14 and the sacrum 16.

In certain embodiments, the orientation of each of the apertures 20 may be generally parallel to each other. In other embodiments, the apertures 20 may be formed in a non-parallel relationship.

For example, the two screws 720 on each side converge toward the safe zone as illustrated in FIGS. 34-38, which are lateral, inlet and outlet fluoroscopic images of the pelvis region. It is to be noted that neither of the bone screws 720 penetrate into the alar scope, which could be caused by the entry point being too cephalad. Such a situation is to be avoided because it can result in complications to the patient, which requires immediate correction.

While the figures only illustrated the procedure being performed on one side of the patient, a person of skill in the art will appreciate that the process may be repeated on the other side of the patient.

While the concepts of the invention are primarily described in conjunction with preparation for a sacroiliac fusion, a person of skill in the art will appreciate that the concepts may be adapted for other joints in the body. The concepts may also be used for preparing an interior region of a bone.

As an alternative to disturbing the surfaces of the ilium 14 and the sacrum 16 to expose bleeding bone, it is possible for the undercutting system to remove more bone from at least one of the ilium 14 and the sacrum 16. Such a process could create a relatively planar prepared region between the ilium 14 and the sacrum 16. Because the ilium 14 and the sacrum 16 are not substantially flat, a greater amount of bone may be removed using such a process. This process obliterates a portion of at least one of the ilium 14 and the sacrum 16.

However, when performing such a process, care should be exercised so that the cutting assembly does not cut all the way through the ilium 14 or the sacrum 16. Additionally, care should be exercised to not remove too much of the ilium 14 or the sacrum 16 as such a process could result in weakening of the ilium 14 or the sacrum 16.

The process associated with this embodiment may require the use of a sharper and/or stronger cutting assembly so that the cutting assembly resists damage when forces needed to cut more deeply into the ilium 14 and sacrum 16 are used.

After the fusion region is prepared, the cut up bone, cartilage and other tissue may be removed from the fusion region using one of the processes described in the other portions of this patent application. A bone growth material may be placed into the fusion region. A bone screw or other fastening device may be used to retain the ilium 14 and the sacrum 16 in a stationary position with respect to each other while bone grows between the ilium 14 and the sacrum 16.

While the concepts of the invention are primarily described in conjunction with preparation for a sacroiliac fusion, a person of skill in the art will appreciate that the concepts may be adapted for other joints in the body. The concepts may also be used for preparing an interior region of a bone.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of performing an orthopedic procedure in the sacroiliac region, the method comprising:
    forming at least one aperture that at least partially extends through at least one of an ilium and a sacrum;
    inserting an undercutting system at least partially into the aperture, wherein the undercutting system comprises an insertion apparatus, a probe assembly and a cutting assembly;
    moving the probe assembly with respect to the insertion apparatus from a retracted position to an extended position, wherein when in the retracted position, the probe assembly is substantially within the insertion apparatus and wherein when in the extended position, at least a portion of the probe assembly extends from the insertion apparatus;
    manipulating the probe assembly within a joint between the ilium and the sacrum while the probe assembly is in the extended position;
    moving the cutting assembly with respect to the insertion apparatus from a retracted position to an extended position, wherein when in the retracted position, the cutting assembly is substantially within the insertion apparatus and wherein when in the extended position, at least a portion of the cutting assembly extends from the insertion apparatus, wherein the cutting assembly is sharper than the probe assembly;
    manipulating the cutting assembly within the joint between the ilium and the sacrum while the cutting assembly is in the extended position to form a fusion region; and
    removing the undercutting system from the aperture.

2. The method of claim 1, wherein the aperture is oriented at an angle of between about 45° and 135° with respect to the at least one of the ilium and the sacrum through which the aperture extends.

3. The method of claim 1, wherein the insertion apparatus is oriented about a central axis and wherein as the cutting assembly moves to the extended position, a distal end of the cutting assembly moves away from the central axis.

4. The method of claim 1, wherein forming the fusion region comprises removing at least a portion of a surface of the ilium and the sacrum with the cutting assembly to produce bleeding bone.

5. The method of claim 1, wherein the cutting assembly extends over at least a portion of the probe assembly.

6. The method of claim 1, wherein the cutting assembly has a cutting surface on at least one edge thereof, wherein the cutting assembly comprises a first cutting assembly and a second cutting assembly, wherein the second cutting assembly has a height that is greater than a height of the first cutting assembly and wherein forming the fusion region comprises:
- positioning the first cutting assembly between the ilium and the sacrum;
- moving the first cutting assembly between the ilium and the sacrum to cut tissue;
- positioning the second cutting assembly between the ilium and the sacrum; and
- moving the second cutting assembly between the ilium and the sacrum to cut tissue.

7. The method of claim 1, and further comprising retaining the sacrum in a stationary position with respect to the ilium by inserting a fastening device into the aperture so that the fastening device engages the ilium and the sacrum, wherein the fastening device is a screw, a peg, a pin, a cage, glue or a coupled device having a ball and a socket.

8. The method of claim 1, wherein the cutting assembly resists movement in a radial direction with respect to the insertion apparatus and wherein the cutting assembly exhibits flexibility in a distal-proximal direction with respect to the insertion apparatus.

9. The method of claim 1, and further comprising a cutting assembly locking mechanism that is movable between a locked configuration and an unlocked configuration, wherein the cutting assembly is retained in a stationary position with respect to the insertion apparatus when the cutting assembly locking mechanism is in the locked configuration and wherein the cutting assembly is rotatable with respect to the insertion apparatus when the cutting assembly locking mechanism is in the unlocked configuration.

10. The method of claim 1, wherein the insertion apparatus further comprises a control portion operably attached thereto proximate a proximal end thereof and wherein the control portion is operably attached to the cutting assembly for moving the probe assembly and the cutting assembly between the extended configuration and the refracted configuration.

11. The method of claim 1, and further comprising removing tissue cut with the cutting assembly from the fusion region.

12. A method of performing an orthopedic procedure in the sacroiliac region, the method comprising:
- forming at least one aperture that at least partially extends through at least one of an ilium and a sacrum;
- inserting an undercutting system at least partially into the aperture, wherein the undercutting system comprises a cutting assembly;
- moving the cutting assembly to an extended position between the ilium and the sacrum where a portion of the cutting assembly extends beyond an outer periphery of the undercutting system;
- forming a fusion region by moving the cutting assembly between the ilium and the sacrum;
- moving the cutting assembly to a retracted position where the cutting assembly is substantially within the outer periphery of the undercutting system;
- removing the undercutting system from the aperture; and
- inserting a fastening device into the ilium aperture and the sacrum aperture, wherein the fastening device retains the ilium and the sacrum in a stationary position with respect to each other.

13. The method of claim 12, wherein the aperture is oriented at an angle of between about 45° and 135° with respect to the at least one of the ilium and the sacrum through which the aperture extends.

14. The method of claim 12, wherein proximate a distal end of the undercutting system, the undercutting system is oriented about a central axis and wherein as the cutting assembly moves to the extended position, a distal end of the cutting assembly moves away from the central axis.

15. The method of claim 12, wherein forming the fusion region comprises removing at least a portion of a surface of the ilium and the sacrum with the cutting assembly to produce bleeding bone.

16. The method of claim 12, wherein the cutting assembly comprises a first cutting assembly and a second cutting assembly and wherein forming the fusion region comprises:
- moving the first cutting assembly between the ilium and the sacrum to cut tissue; and
- moving the second cutting assembly between the ilium and the sacrum to cut tissue, wherein the second cutting assembly extends over at least a portion of the first cutting assembly, wherein the second cutting assembly is sharper than the first cutting assembly and wherein the second cutting assembly has a height that is greater than a height of the first cutting assembly.

17. The method of claim 16, wherein:
- moving the first cutting assembly between the ilium and the sacrum causes the first cutting assembly to extend into an intra-articular region between the ilium and the sacrum; and
- moving the second cutting assembly between the ilium and the sacrum comprises:
  - cutting tissue between the ilium and the sacrum; and
  - removing at least a portion of a surface of the ilium and the sacrum to produce bleeding bone.

18. The method of claim 12, wherein the fastening device is a screw, a peg, a pin, a cage, glue or a coupled device having a ball and a socket and wherein the fastening device is the same as the first fastening device.

19. The method of claim 12, wherein the undercutting system further comprises an insertion apparatus and wherein the cutting assembly is operably attached to the insertion apparatus.

20. The method of claim 19, wherein the undercutting system further comprises a cutting assembly locking mechanism, wherein the cutting assembly locking mechanism is movable between a locked configuration and an unlocked configuration, wherein the cutting assembly is retained in a stationary position with respect to the insertion apparatus when the cutting assembly locking mechanism is in the locked configuration and wherein the cutting assembly is rotatable with respect to the insertion apparatus when the cutting assembly locking mechanism is in the unlocked configuration.

21. The method of claim 19, wherein the insertion apparatus further comprises a control portion operably attached thereto proximate a proximal end thereof and wherein the control portion is operably attached to the cutting assembly for moving the cutting assembly between the extended configuration and the retracted configuration.

* * * * *

UNITED STATES PATENT AND TRADEMARK OFFICE
CERTIFICATE OF CORRECTION

| | |
|---|---|
| PATENT NO. | : 9,662,124 B2 |
| APPLICATION NO. | : 14/721753 |
| DATED | : May 30, 2017 |
| INVENTOR(S) | : Robert Assell et al. |

It is certified that error appears in the above-identified patent and that said Letters Patent is hereby corrected as shown below:

In the Specification

In Column 25, Line 55, "refraction" should be --retraction--

In Column 33, Line 24, "refraction" should be --retraction--

In Column 34, Line 4, "refracted" should be --retracted--

In the Claims

In Column 41, Claim 10, Line 6, "refracted" should be --retracted--

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*